(12) United States Patent
Liu et al.

(10) Patent No.: US 11,732,254 B2
(45) Date of Patent: Aug. 22, 2023

(54) SIZE SELECTION PURIFICATION USING A THERMOPLASTIC SILICA NANOMATERIAL

(71) Applicant: CIRCULOMICS, INC., Baltimore, MD (US)

(72) Inventors: Kelvin Jeng-Fang Liu, Baltimore, MD (US); John Duncan Kilburn, Baltimore, MD (US); Jeffrey Michael Burke, Baltimore, MD (US)

(73) Assignee: Pacific Biosicences of California, Inc., Menlo Park, CA (US)

( * ) Notice: Subject to any disclaimer, the term of this patent is extended or adjusted under 35 U.S.C. 154(b) by 0 days.

(21) Appl. No.: 16/627,578

(22) PCT Filed: Jun. 29, 2018

(86) PCT No.: PCT/US2018/040324
§ 371 (c)(1),
(2) Date: Dec. 30, 2019

(87) PCT Pub. No.: WO2019/006321
PCT Pub. Date: Jan. 3, 2019

(65) Prior Publication Data
US 2020/0255822 A1    Aug. 13, 2020

Related U.S. Application Data

(60) Provisional application No. 62/527,659, filed on Jun. 30, 2017.

(51) Int. Cl.
*C12N 15/10* (2006.01)
*B01J 20/10* (2006.01)

(52) U.S. Cl.
CPC .......... *C12N 15/1017* (2013.01); *B01J 20/10* (2013.01)

(58) Field of Classification Search
CPC .... C12N 15/1017; G01N 33/552; C12Q 1/68; B01J 20/283; B01J 20/286; B01J 21/08; B01J 20/10
See application file for complete search history.

(56) References Cited

U.S. PATENT DOCUMENTS

| | | | |
|---|---|---|---|
| 2005/0208510 A1* | 9/2005 | Latham | C12N 15/1013 435/6.12 |
| 2010/0323913 A1 | 12/2010 | Young et al. | |
| 2011/0313145 A1 | 12/2011 | Sharon et al. | |
| 2012/0083600 A1 | 4/2012 | Felo et al. | |
| 2014/0272944 A1 | 9/2014 | Gundling | |
| 2015/0037802 A1* | 2/2015 | Wang | B01J 20/261 435/6.12 |
| 2015/0166592 A1 | 6/2015 | Guo | |
| 2015/0184255 A1 | 7/2015 | Cai et al. | |
| 2015/0275282 A1 | 10/2015 | Heller et al. | |
| 2016/0046987 A1* | 2/2016 | Kim | C40B 40/06 506/16 |
| 2016/0115471 A1 | 4/2016 | Kim et al. | |
| 2017/0096660 A1 | 4/2017 | Wang et al. | |

FOREIGN PATENT DOCUMENTS

| | | |
|---|---|---|
| CN | 101684138 A | 3/2010 |
| CN | 104350152 A | 2/2015 |
| CN | 105120986 A | 12/2015 |
| CN | 105518120 A | 4/2016 |
| CN | 106460040 A | 2/2017 |
| CN | 106574266 A | 4/2017 |
| CN | 107405540 A | 11/2017 |
| WO | WO 013181651 * | 12/2013 |
| WO | 2014/122288 A1 | 8/2014 |
| WO | 2016/0123101 A1 | 8/2016 |
| WO | 2016/123101 A1 | 8/2016 |
| WO | 2016123101 A1 | 8/2016 |
| WO | 2016/193490 A1 | 12/2016 |
| WO | 2016193490 A1 | 12/2016 |

OTHER PUBLICATIONS

Kim et al, A simple and rapid method for isolation of high quality genomic DNA from fruit trees and conifers using PVP, 1997, Nucleic Acids Research, 25, 1085-1086. (Year: 1997).*
Puchooa, A simple, rapid and efficient method for the extraction of genomic DNA from lychee (Litchi chinensis Sonn.), 2004, African Journal of Biotechnology, 3, 253-255. (Year: 2004).*
Lundin et al, Increased Throughput by Parallelization of Library Preparation for Massive Sequencing, 2010, PLoS One, 5, e10029, pp. 1-7 (Year: 2010).*
Puchooa et al, Genomic DNA Extraction From Victoria amazonica, 2004, Plant Molecular Biology Reporter, 22, 195a-195j (Year: 2004).*
Hanania et al , An Improved Method for Isolating High-Quality DNA From Vitis vinifera Nuclei, 2004, Plant Molecular Biology Reporter 22: 173-177 (Year: 2004).*
International Preliminary Report on Patentability dated Jan. 10, 2020 in corresponding PCT Application No. PCT/US2018/040324, 24 pages.
International Search Report and Written Opinion of the International Searching Authority, dated Sep. 14, 2018, in corresponding International Application No. PCT/US2018/040324, 11 pages.
Extended European Search Report and Supplemental ESR and European Search Opinion dated Feb. 26, 2021 in corresponding European Application No. 18823442.1, 6 pages.

(Continued)

*Primary Examiner* — Narayan K Bhat
(74) *Attorney, Agent, or Firm* — MH2 Technology Law Group, LLP; Timothy M. Hsieh

(57) ABSTRACT

The present disclosure is directed to a method for purifying a sample containing nucleic acids to obtain isolated nucleic acids of a desired size range, either above a size cut-off, below a cut-off, or within a defined band of sizes, including: a) combining a nucleic acid-containing sample with a binding buffer to provide a binding mixture; b) contacting the binding mixture with a silica nanomembrane, wherein the silica nanomembrane adsorbs nucleic acids from the binding mixture within a desired size-range; and c) separating the bound nucleic acid from the remaining sample. Kits including a silica nanomembrane, a binding buffer and one or wash buffers are also provided herein.

31 Claims, 9 Drawing Sheets

(56) References Cited

OTHER PUBLICATIONS

Liu et al., "High-Throughput, High MW DNA Extractions and Size Selection for Long-Read Sequencing," Poster Abstracts, Journal of Biomolecular Techniques, vol. 30, Supplement, 2019, p. S19.
Timp, "Extracting DNA for Nanopore Sequencing in the Redwood Genome Project," Nanopore Community Meeting 2017, Oxford Nanopore Technologies, 19 pages.
Zhang et al., "A Simple Thermoplastic Substrate Containing Hierarchical Silica Lamellae for High-Molecular-Weight DNA Extraction," Advanced Materials, 2016, 28, 10630-10636.
"Notification of Reasons for Rejection" dated Dec. 14, 2021 in corresponding Japanese Application No. 2019-572747 (English translation provided), 8 pages.
Eid et al., "Real-Time DNA Sequencing from Single Polymerase Molecules," Science, vol. 323 (2009) 133.
Ellis, "Macromolecular crowding: obvious but underappreciated," Trends in Biochemical Sciences, vol. 26, No. 10, Oct. 2001.
Jain et al., "The Oxford Nanopore MinION: delivery of nanopore sequencing to the genomics community," Genome Biology (2016) 17:239.
Lam et al., "Genome mapping on nanochannel arrays for structural variation analysis and sequence assembly," Nat. Biotechnol., Aug. 2012, 30(8).
Liu et al., "Size-selective separation of DNA fragments by using lysinefunctionalized silica particles," Scientific Reports, 6:22029, Feb. 25, 2016, 8 pages.
Raspaud et al., "Precipitation of DNA by Polyamines: A Polyelectrolyte Behavior," Biophysical Journal, vol. 74, Jan. 1998, 381-393.
Tian et al., :Evaluation of Silica Resins for Direct and Efficient Extraction of DNA from Complex Biological Matrices in a Miniaturized Format, Analytical Biochemistry, 283 (2000) 175-191.
Vandeventer et al., "Multiphasic DNA Adsorption to Silica Surfaces under Varying Buffer, pH, and Ionic Strength Conditions," J. Phys. Chem B. (2012) 116(19), 5661-5670.
Zhang et al., "A Simple Thermoplastic Substrate Containing Hierarchical Silica Lamellae for High Molecular Weight DNA Extraction," Adv. Mater. Dec. 2016, 28(48).
Zheng et al., "Haplotyping germline and cancer genomes using high-throughput linked-read sequencing," Nat. Biotechnol. Mar. 2016, 34(3).
Zhou et al., "Macromolecular crowding and confinement: biochemical, biophysical, and potential physiological consequences," Annu Rev. Biophys. 2008, 37, 375-397.
Melzak et al., "Driving Forces for DNA Adsorption to Silica in Perchlorate Solutions," Journal of Colloid and Interface Science, 181 (1996), 635-644.

\* cited by examiner

SIZE SELECTION PURIFICATION USING A THERMOPLASTIC SILICA NANOMATERIAL

CROSS-REFERENCE TO RELATED APPLICATIONS

This application is a U.S. National Stage application of International Application No. PCT/US2018/040324, filed 29 Jun. 2018, which claims the benefit of priority from U.S. Provisional Patent Application No. 62/527,659, filed 30 Jun. 2017, the entire disclosures of which are hereby incorporated by reference in their entireties.

BACKGROUND

In recent years, 3rd generation sequencing technologies have revolutionized our understanding of the structure-function of the genome and the accuracy of reference assemblies. Transformative advances from Pacific Biosciences[1] (Menlo Park, Calif.), Oxford Nanopore Technologies Limited[2] (Oxford, United Kingdom), 10× Genomics[3] (Pleasanton, Calif.) and BioNano Genomics[4] (San Diego, Calif.) have created a resurgent need for high molecular weight (HMW) DNA of the utmost quality and for new technologies to effectively process it. However, the vast majority of technologies to process and analyze HMW DNA, such as pulsed field gel electrophoresis (PFGE), precipitation and gel plug extractions and dialysis purification were originally developed in the infancy of molecular biology and are incredibly slow and tedious.

Library preparation for most long-read sequencing technologies follows a similar workflow. First, HMW DNA (50 kb-Mb+) must be isolated. Next, the DNA is prepared for sequencing using various enzymatic steps. During enzymatic processing, size selection is used to remove smaller background molecules from the desired library products. This is done almost exclusively with Beckman Coulter AMPURE® beads. However, AMPURE® has low recovery efficiency (<25%) for HMW DNA due to bead entanglement, preferentially losing the longest, most desired DNA molecules. This problem is exacerbated as libraries grow longer and in library preparations requiring multiple AMPURE® steps. Furthermore, the size selection cutoffs for AMPURE® (100 bp-1000 bp) are too low for most long-read libraries. Thus, a follow-up size selection is often performed using a PFGE instrument such as Sage Science's BLUEPIPPIN™ (Beverly, Mass.) to enhance read lengths by isolating only the highest molecular weight library products. While BLUEPIPPIN™ can size select large DNA (100 bp-50 kb), it is slow (8.5 hours) and also damages DNA during the long PFGE process, necessitating subsequent enzymatic repair. All size selection steps must work optimally at relatively high concentrations (>50 ng/μl); as sequencing lengths desired increase, the mass concentration of DNA must also increase in order to keep a constant molarity. Thus, for reads in the range 100 kbp to 1 Mbp the mass concentration needs to be 200-3000 times higher than samples with the same molarity that have fragment lengths of 350-600 bp typical of Illumina sequencing. The recoveries of both AMPURE® and BLUEPIPPIN™ are impaired at high concentrations.

Accordingly, there remains a desire in the art for technologies capable of rapid size selection of both small and large nucleic acid molecules that does not require separate AMPURE® and PFGE purification steps and which does not damage the nucleic acids during processing.

SUMMARY

The present disclosure is directed to methods for purifying a sample containing nucleic acids to obtain isolated nucleic acids of a desired size range including: a) combining a nucleic acid-containing sample with a binding buffer to provide a binding mixture; b) contacting the binding mixture with a nanomembrane (e.g., a silica nanomembrane or the like), wherein the nanomembrane binds nucleic acids in the binding mixture (e.g., within a desired size range); c) selecting the nucleic acids based on size prior to, during, or after binding the nucleic acids with the nanomembrane; and d) separating the bound nucleic acids from the remaining sample. In some embodiments, proteins are co-purified with the nucleic acids.

In some embodiments, step c) comprises washing the nanomembrane after nucleic acid binding to selectively remove nucleic acids of a specific size range. In certain embodiments, step c) comprises selectively binding nucleic acids of a specific size range. Optionally, step c) comprises selectively eluting bound nucleic acids of a specific size range. In some embodiments, step c) comprises performing a size specific precipitation of nucleic acids prior to step a). In some embodiments, step c) comprises performing a size specific precipitation of nucleic acids during nucleic acid binding. In certain embodiments, step c) comprises performing a size specific precipitation of nucleic acids after elution. Optionally, step c) comprises two or more size selective steps used in combination or sequentially.

In certain embodiments, the nucleic acids of the desired size range are bound to the nanomembrane, whereas in other embodiments, the nucleic acids of the desired size range are not bound to the nanomembrane. Typically, the nanomembrane comprises a nanomembrane, and the method comprises a) contacting a wash solution with the nanomembrane, and b) removing the wash solution from contact with the nanomembrane.

In certain embodiments, the desired size range of nucleic acids comprises all sizes above a cutoff value, whereas in other embodiments, the desired size range of nucleic acids comprises all sizes below a cutoff value. In some embodiments, the desired size range of nucleic acids is a size range band above a lower cutoff value and below an upper cutoff value. Optionally, nucleic acids of a specific size band are produced by two or more sequential purification steps. In some embodiments, a first eluate comprising nucleic acid sizes below a cutoff value and a second eluate comprising nucleic acid sizes above a cutoff value are produced from a single nucleic acid-containing sample.

Typically, the methods include selectively binding nucleic acids of a specific size range, determined by at least one binding condition, wherein at least one binding condition is selected from the group consisting of:
 a. pH,
 b. salt concentration,
 c. presence or absence of chaotropic salts,
 d. presence or absence of monovalent and/or divalent salts,
 e. alcohol type and concentration,
 f. molecular crowder concentration,
 g. type and molecular weight of molecular crowder,
 h. binding time,
 i. temperature during binding,
 j. presence or absence of denaturing agents, k. presence or absence of polyamines,
l. presence or absence of other additive molecules,
m. buffer volume,
n. motion of tube during binding, for example vortexing, centrifugation, shaking, rotating,
o. size of nanomembrane,
p. shape of nanomembrane,
q. 3D conformation of nanomembrane,
r. number of nanomembranes, and
s. combinations thereof.

In some embodiments, size specific precipitation is facilitated by at least one condition of a precipitation buffer, wherein the at least one condition of the precipitation buffer is selected from the group consisting of:
a. molecular crowder concentration,
b. molecular crowder molecular weight,
c. molecular crowder type,
d. presence or absence of chaotropic salts,
e. presence or absence of monovalent and/or divalent salts,
f. salt concentration and type,
g. alcohol type and concentration,
h. the presence or absence of polyamines,
i. the presence or absence of denaturing agents,
j. the presence or absence of other additive molecules,
k. pH,
l. precipitation/binding time,
m. precipitation/binding temperature,
n. precipitation/binding volume,
o. centrifugation time,
p. centrifugation temperature, and
q. combinations thereof.

In certain embodiments, wherein the nanomembrane is functionalized with one or more groups selected from the group consisting of:
a. aminopropyl,
b. chloropropyl,
c. octadecyl,
d. octyl,
e. quaternary ammonium groups,
f. diethylaminoethyl groups,
g. sulfonic acid groups,
h. sulfhydryl,
i. thiol groups,
i. carboxyl groups,
k. hydroxyl groups,
l. phenyl groups,
m. aldehyde groups,
n. silanes,
o. halides,
p. chitosan,
q. biotin,
r. streptavidin,
s. lectin,
t. antibodies,
u. proteins,
v. enzymes,
w. amino acids,
x. oligonucleotides,
y. lipids,
z. polyethylene glycol,
aa. dextran, and
bb. polymers.

Also provided herein is a kit for purifying a sample containing nucleic acids to obtain isolated nucleic acids of a desired size range including a nanomembrane disks, a binding buffer, and one or more wash buffers. In some embodiments, the binding buffer comprises a molecular crowder (e.g., polyethylene glycol, polyvinylpyrrolidone, or the like). In certain embodiments, the one or more wash buffers comprises isopropyl alcohol.

BRIEF DESCRIPTION OF THE FIGURES

FIG. 1A depicts scanning electron microscope (SEM) images of a NANOBIND™ surface showing hierarchical layering of microscale folds and nanoscale silica lamella that can be fine-tuned based on $SiO_2$ thickness (top—20 nanometers (nm) $SiO_2$, bottom—150 nm $SiO_2$, left—low magnification, right—high magnification). FIG. 1B depicts fabrication of Magnetic NANOBIND™ and NANOBIND™ disks through a heat shrinking process that may be scaled for low cost. FIG. 1C depicts methods of nucleic acid extraction using manual (top) and automated (bottom) platforms. FIG. 1D depicts binding, washing and elution of nucleic acids using NANOBIND™, which parallel protocols used with magnetic particles and spin columns. Processing typically takes as few as 15 minutes. FIGS. 1A-1D are further described in the detailed description.

DETAILED DESCRIPTION

Figure 1B:
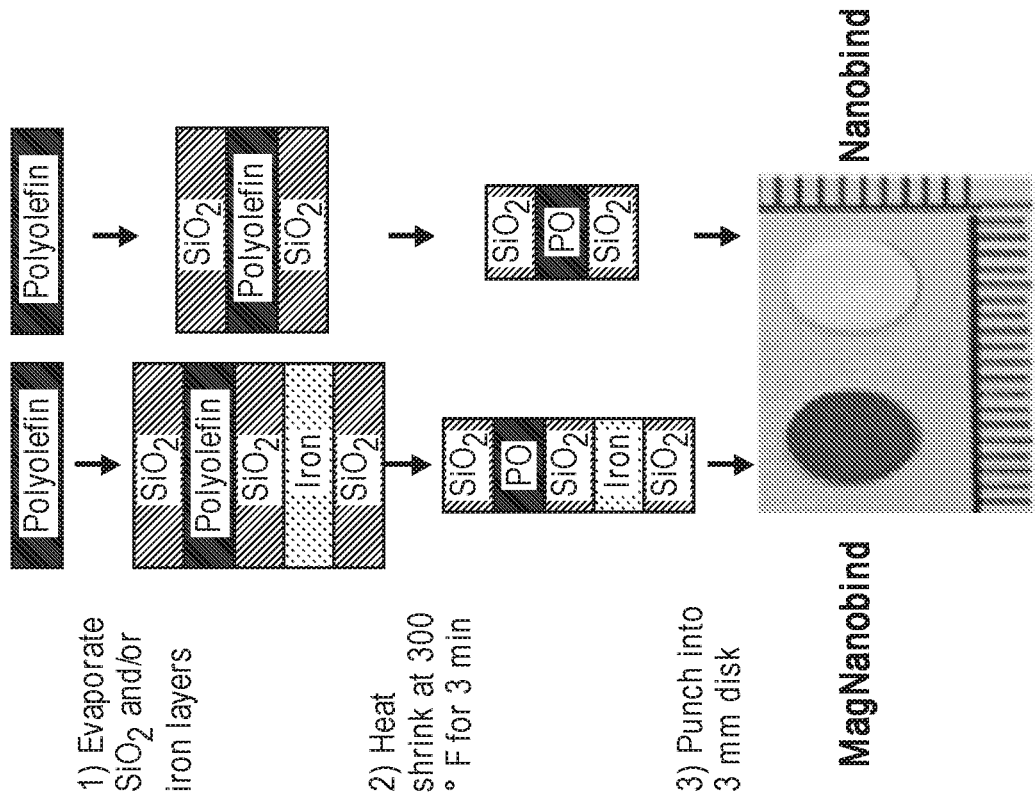
FIGS. 1A-1D.

The present disclosure is directed to methods for the rapid size selection of both small and large size nucleic acid molecules from nucleic acid-containing samples using nanomembrane, such as NANOBIND™. Nanomembranes, such as NANOBIND™, are novel thermoplastic nanomaterials that can be inexpensively manufactured and are generally capable of extracting higher quality nucleic acids from nucleic acid-containing samples than are other nucleic acid binding matrices. See, for example, Reference 5, which is hereby incorporated by reference in its entirety. The low shear, non-porous substrate of a nanomembrane employs a novel tentacle binding mechanism that condenses nucleic acid, such as DNA, onto the surface of, for example, a disk, and protects it from fragmentation and other damage allowing for the extraction and/or purification of high quality, high MW DNA. Due to the unique condensation based binding mechanism, the binding properties of a nanomembrane can be fine-tuned to impart a wide range of nucleic acid size selection capabilities. Using silica nanomembranes such as NANOBIND™, the present inventors were able to size select both small and large nucleic acids at high efficiency allowing for the replacement of inefficient AMPURE® purifications and slow gel separations, for example, with a single bind, wash, and elute process as described herein.

Next generation sequencing (NGS) is experiencing tremendous growth driven by both research and clinical applications. $3^{rd}$ generation sequencing technologies are being used to de novo sequence an ever-growing catalog of plants, animals, and microbes while continually refining the quality of human reference genomes. NGS is also being used to better understand fundamental biology such as genetic diversity, metagenomics, and epigenetics. However, the maturation of clinical tests such as liquid biopsies, non-invasive prenatal testing, and infectious disease testing will likely grow to be the major driving force in the near future.

Size selection purification is an integral part of NGS library preparation, with some preps requiring as many as 10 purification steps, using a combination of spin columns, magnetic particles, and gel purification to cleanup enzymatic reactions and to ensure that only properly prepared library molecules are sequenced. Typically, size selection purification is first used to remove small molecules such as adapter dimers, oligos, enzymes, and salts from the properly prepared library molecules. In some cases, double purifications are necessary to ensure sufficient removal of adapter dimers. A second size selection step is often used to further isolate only library molecules of a specific size. The large number of purification steps means that high recovery is paramount. In short-read NGS, poor size selection can prevent accurate alignment and assembly, particularly in methods such as mate pair sequencing. In long-read NGS, excess short DNA compromises mean read lengths and reduces assembly quality.

No current technique can satisfy all of the above size selection needs (Table 1). Beckman Coutler AMPURE® magnetic particles are widely used due to their ease of processing, tunable cutoffs (100 bp-1 kb), and automation capability. Spin columns can also be used but have low cutoffs (150 bp) and are not tunable, limiting their application. For NGS applications requiring higher cutoffs, such as long-read and mate pair sequencing, gel purification is the only method despite being exceedingly tedious, slow, and highly variable. Size Selection using nanomembranes is the only technology that offers the speed of magnetic particles with the flexible sizing capabilities of gel purification to address multiple purification steps in NGS library preparation.

To further illustrate, Table 1 shows that the NANOBIND size select purification method eliminates the need to use disparate methods for NGS library purification. It has 100× higher sizing cutoff than AMPURE® particles to rival gel purification. It removes up to 20× more small molecules than AMPURE® to eliminate the need for sequential purifications. It has high recovery efficiency for DNA libraries of all sizes and fast processing.

TABLE 1

| Product | Format | Size Selection Range | Recovery Efficiency | Purification Efficiency | Time |
|---|---|---|---|---|---|
| Circulomics Nanobind Size Select | Magnetic Disk | 100 bp-100 kb | 80-99% for all DNA sizes | 99% | 20 min-1 h |
| Beckman Coulter AMPURE XP | Magnetic Particle | 100 bp-1 kb | 80-99% for small DNA <34% for HMW DNA | 80-99% | 20 min |
| Qiagen GeneRead Size Select | Spin Column | 150 bp only | N/A | N/A | 15 min |
| Sage Science Blue Pippin | Gel Purification | 100 bp-50 kb | 50-80% <30 ± 23% for HMW DNA | N/A | 1-8.5 hr |

NANOBIND™ is a nucleic acid sample preparation technology that offers numerous benefits over traditional columns and magnetic particles. Rather than a porous membrane or millions of individual microparticles, NANOBIND™ is a solid magnetic disk (1-5 mm diameter) covered with a high density of micro- and nanostructured silica. The disks are inexpensively manufactured from heat shrink film using industrial roll-to-roll processes at a cost of pennies per disk. The nanostructured disk format enables unparalleled binding capacity, DNA quality, and purity. A single disk can bind over 10 milligrams of DNA, hundreds of times more than comparable column and particle methods. The disk format also protects DNA from damage enabling rapid extraction of high molecular weight (MW) DNA from a variety of samples including cells, bacteria, blood, and plants. It is the only solid phase technology capable of extracting ultra high MW megabase DNA that is of sufficient quality for genome mapping. Processing occurs through a bind, wash, and elute process that can be performed manually or automated using common instruments. The high DNA quality leads to exceptional sequencing data on platforms including PacBio and Oxford Nanopore. The disk format also eliminates fluidic dead volume, leading to higher purity through more efficient washing and minimized contaminant carryover. Furthermore, by reducing the size of the NANOBIND™ disk and buffer volumes, samples as small as 1 µL and 10 cells can be efficiently processed. These properties enable the NANOBIND™ disk to achieve wider size selection capability, higher yield, and higher purity than any magnetic particle or spin column system.

As also described herein, the novel tentacle binding mechanism employed in order to perform a DNA size selection with a nanomembrane, such as NANOBIND™, results in a number of significant differences between its performance and the performance of existing prior art methods, such as AMPURE® or spin columns. The nucleic acid binding to the nanomembrane is primarily driven by precipitation forces; the nanomembrane acts as a precipitation seed whereby DNA condenses onto the surface of the NANOBIND™ disk. The majority of DNA nucleic acid molecules are bound to other nucleic acid molecules rather than the disk itself. A small fraction of the nucleic acid molecules anchor the rest of the precipitated molecules to the nanomembrane. This mechanism means that the precipitation conditions can be adjusted so that the size cutoff between nucleic acids that precipitate and subsequently bind and those that do not can be changed to higher molecular weights than with AMPURE® beads. This approach is possible with NANOBIND™ due to the micro- and nano-structured surface which acts as an efficient seed for DNA condensation and a non-porous tether for precipitated DNA to tightly tether and subsequently release. This approach is not possible with AMPURE® beads as it results in insoluble DNA entanglements of magnetic beads and DNA, where DNA cannot be eluted. Such an approach is also not possible with spin columns as the precipitated DNA would clog the column.

Thus, Size Selection using nanomembranes has a 100× wider range of cutoffs (100 bp-100 kb) than any magnetic particle or column method. Size Selection using nanomembranes also had up to 5× higher recovery of the high MW gDNA libraries than both magnetic particles and automated gel purification, reducing reagent cost and sample input by >50%. At the same time, NANOBIND™ has higher purification efficiency with up to 19× less adapter dimer contamination, reducing wasted sequencing reads. Finally, Size Selection using nanomembranes was 8.5× faster than gel purification, replacing the slow 8.5 hr. BluePippin purification with a rapid <1 hr. bind, wash, and elute process.

In addition to being used for NGS library preparation processes of size selection using nanomembranes can be used for PCR purification, enzymatic reaction cleanup, or any application where nucleic acid molecules need to be separated based on size.

As also described herein, the Small Size Select process using a nanomembrane, such as NANOBIND™, results in tunable cutoffs of nucleic acids ranging in size between 10 bp-30000 bp. The Small Size Select process can eliminate small molecules below the cutoff, such as dNTPs, excess primers, enzymes, and reaction side products such as primer dimers, while recovering library products above a cutoff value, including high MW DNA. High purification efficiency (>99.9%) can be obtained while maintaining superior recovery (e.g., >90%) of high MW DNA (e.g., 50 kb-1 Mb+) in comparison to the purification efficiency and recovery of nucleic acids obtained using other methods, such as those using AMPURE® or spin columns.

As also described herein, a Large Size Select process using a nanomembrane, such as NANOBIND™, results in tunable cutoffs of nucleic acids ranging in size between 200 bp-100 kb. The Large Size Select process can be used to eliminate nucleic acid molecules below the cutoff, for example, to obtain sequencing libraries for enhanced sequencing read lengths. As described herein below, molecular crowding may be used to separate the undesired short library products from the desired long library products and to speed library preparation by replacing slow and tedious PFGE separation with an instant rapid bind, wash, and elute process. High purification efficiency (e.g., >99%) across, e.g., the 200 bp-100 kb range can be achieved with high efficiency recovery (e.g. >90%) of high MW DNA (e.g., 50 kb-1 Mb+) rapidly, e.g., <1 hour process. In contrast, no other magnetic particle or spin column technology is capable of size selection in the kilobase range.

As also described herein, a number of size selection procedures can be performed sequentially to allow a band of DNA sizes between a minimum and a maximum to be selected. This can be e.g., a combination of two small size selections, two large size selections, or a small size selection followed by a large size selection, or a large size selection followed by a small size selection.

As also described herein, size depletion can be used to remove nucleic acids above a cutoff. This is achieved by first performing large or small size selection using a nanomembrane on a sample and then taking the binding buffer which contains unbound nucleic acids below a cutoff and performing a second nanomembrane purification to recover this nucleic acid.

As also described herein proteins can be co-purified with nucleic acid. The aim of most purifications methods is to take a reaction mixture and return only the size selected nucleic acid fraction whilst removing all other reagents, including but not limited to enzymes, buffers and dNTPs. As described herein, methods which allows nucleic acid and proteins to be purified together in some embodiments such that both nucleic acids and enzymes, for example, can be isolated from the rest of the reagents in a co-purification.

Method for Isolating Nucleic Acids

The present disclosure describes methods that include, for example, silica nanomembranes for binding, e.g., adsorbing, nucleic acids as described herein. As used herein, the term "nanomembranes" refers to three-dimensional conformations of silica, metals, or other layers on a polymer core, which can comprise structures such as micro-wrinkles, nano-wrinkles and flakes, ranging from tens of nanometers to micrometers in size. The terms "lamella", "wrinkle", "fold", "flake", "chip", and the like are descriptive terms used to describe the appearance of such structures on the nanomembrane surface. These three-dimensional structures are created as a result of stress induced by heat shrinking of the polymer core. See e.g., FIG. 1A for an example of silica nanomembrane topography.

The nanomembrane may comprise additional layers or coatings to impart additional properties. For example, a magnetic layer such as iron, nickel, or permalloy may be deposited, e.g. beneath, on top, or between silica layers, to enable e.g., manipulation of the nanomembranes with a magnet.

The nanomembrane may be coated with silica and be referred to as a silica nanomembrane. The term "silica" as used herein means silicon oxide, silicon dioxide and silicon dioxide derivatives, such as $SiO_2$ crystals and other forms of $SiO_2$, for example diatoms composed of $SiO_2$, zeolites, amorphous silicon dioxide, glass powder, silicic acid, waterglass, quartz, borosilicate, and also aluminum silicates and activated silicates. Nanomembranes may contain no actual silica but instead be covered with silica-like polymers or coatings such as silanes, silanol-functionalized dextran, silanols, or siloxanes to achieve the same functionality.

Additionally, the surface may be functionalized or coated with other groups to enhance the size selective binding and release properties of the nanomembrane. Functionalization can include but is not limited to aminopropyl groups, chloropropyl groups, octadecyl groups, octyl groups, quarternary ammonium groups, diethylaminoethyl groups, sulfonic acid groups, sulfhydryl groups, thiol groups, carboxylic acid groups, hydroxyl groups, amine groups, aldehyde groups, phenyl groups, silanes, halides, chitosan, biotin, streptavidin, lectin, antibodies, proteins, enzymes, amino acids, oligonucleotides, lipids, polyethylene glycol, dextran, and other polymer molecules. Functionalization of the surface with, for example, amine groups can be used to drive size selection by changing the mode of binding of the DNA to the nanomembrane. At low pH, amine groups are positively charged and so will electrostatically bind DNA molecules. Larger DNA molecules have more possible points of contact to amine groups, and therefore binding points, than smaller DNA molecules. Thus, the net binding force experienced by larger DNA molecules is larger than for small molecules in way that is pH dependent, mediated by the amine functional group. In this way, functional groups can be used to change the size selection properties of nanomembrane DNA purification. Functionalization of a silica surface with the amino acid lysine has been shown to be an effective way to perform size selective purification on DNA samples[6]. More generally, the different functional groups change the mode of binding of DNA to the nanomembrane, which leads to different ways of adjusting their size selection properties.

As used herein, the term "polymer" means any polymer substrate that is capable of heat shrinkage. In some embodiments, the polymers are thermoplastic polymers. As used herein, the term "thermoplastic" means a polymer that becomes pliable or moldable above a specific temperature and returns to a solid state upon cooling. Thermoplastics can include, for example, polymers such as polymethyl methacrylate (PMMA), polycarbonate, polystyrene (PS), polyolefins (PO), cyclic polyolefin (PO), Polyvinyl chloride (PVC), polytetrafluoroethylene, polycarbonate, and polyamide polymers.

As used herein, the term "binding" means the reversible, or irreversible immobilization of (DNA) molecules close to the surface of a nanomembrane. This can encompass, but is not limited to, adsorption, physisorption, chemisorption, electrostatic attraction, covalent bonding and topological entanglement.

Figure 1A:
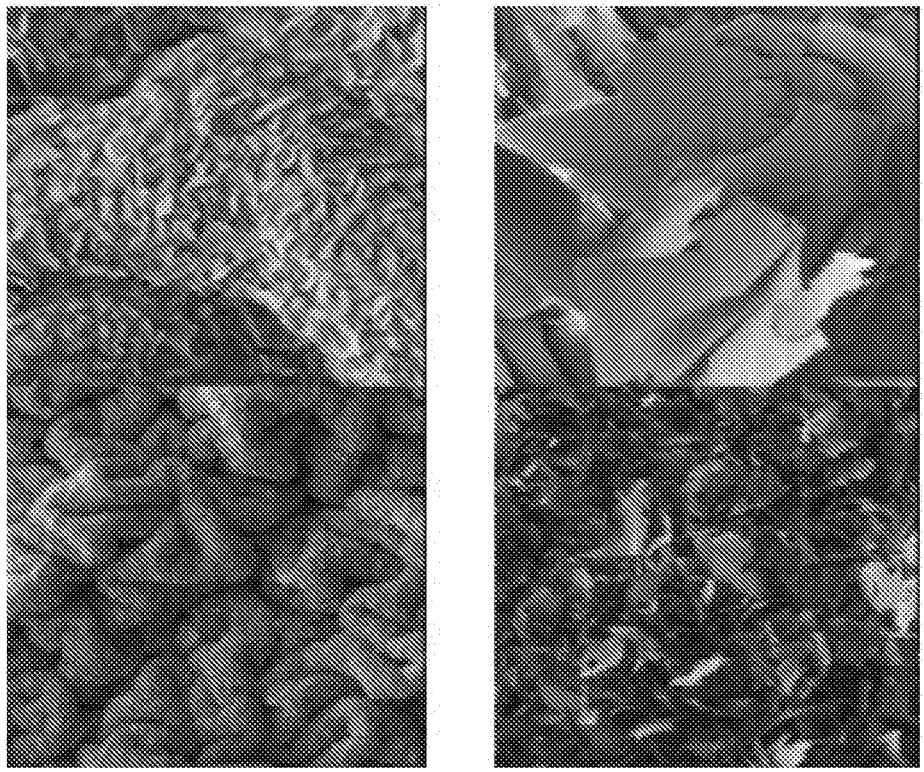
Figure 1D:
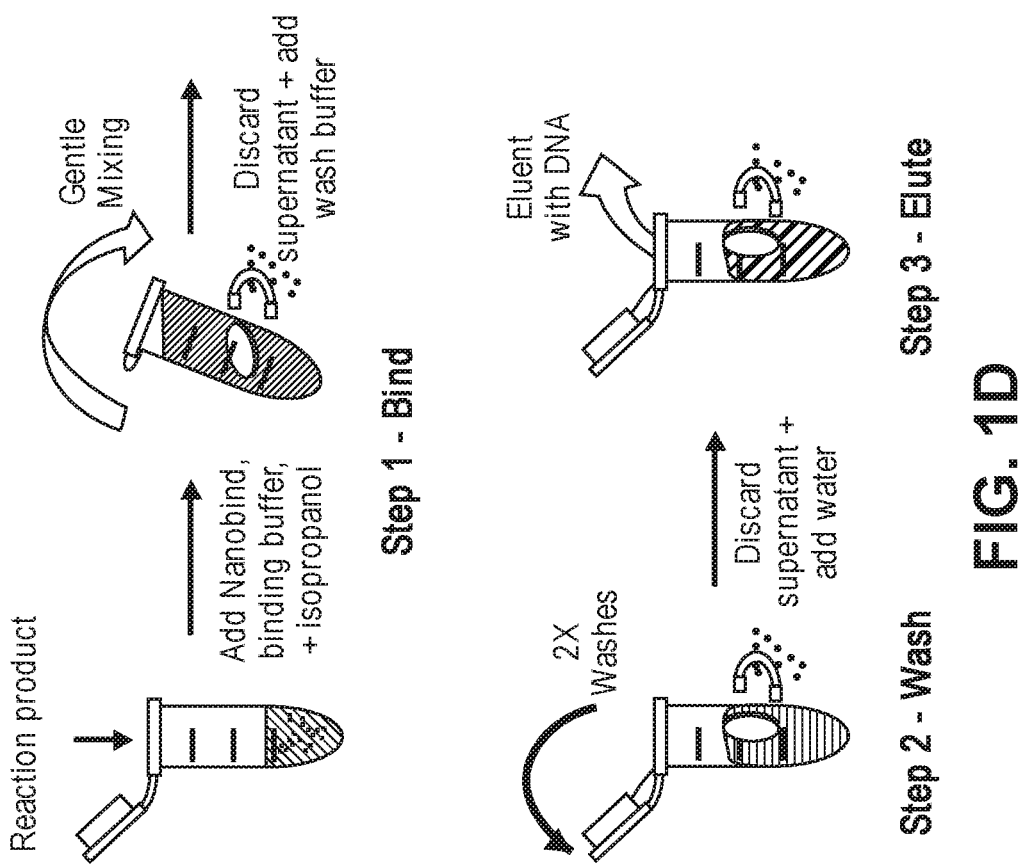
Figure 1C:
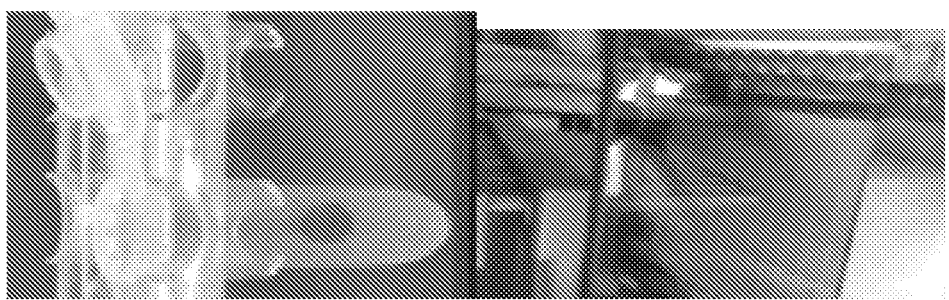

An example of a suitable nanomembrane of the present disclosure includes NANOBIND™ silica nanomembranes (Circulomics Inc., Baltimore, Md.). The nanomembranes of the present disclosure, such as NANOBIND™[5] can be inexpensively manufactured. Reference 5 is hereby incorporated by reference in its entirety. For example, the silica nanomembranes may be fabricated by silicon dioxide deposition, heat shrinkage, and die punching (FIG. 1B). Film deposition is inexpensive and easily scaled using industrial roll-to-roll processes akin to Mylar sheeting that can fabricate hundreds of meters of material per day (millions of extractions) at <$0.01 per extraction7. In some embodiments, the nanomembranes may be magnetized for either manual or automated processing (FIG. 1C). Processing may occur through a bind, wash, and elute protocol as described herein that may be performed in as few as 15 minutes (FIG. 1D). In some embodiments, the nanomembranes may be punched into disks or other shapes to facilitate processing.

In certain embodiments, nanomembranes such as NANOBIND™ are capable of size selection via a novel tentacle binding mechanism. Reference 5 is hereby incorporated by reference in its entirety. Unlike other technologies where nucleic acid binds in a prone conformation and is scattered across microparticles or throughout a porous membrane, NANOBIND™'s low shear, non-porous structure, for example, condenses nucleic acid onto the surface of a disk, for example, in a single macromolecular complex, protecting it from fragmentation and other damage, to generate high quality, high molecular weight nucleic acids as described herein. Binding is driven by condensation of nucleic acid onto a disk, for example, which in turn is driven by myriad molecular forces[8-10] including solubility, electrostatic interactions, salt bridging, and entropy. It is this unique condensation-driven binding mechanism that enables size selection purification across a wider range of nucleic acid sizes than any existing technologies. By changing the purification buffer conditions, the propensity of small vs. large DNA to condense and bind onto the nanomembrane surface can be fine-tuned. See also WO 2016/123101 A1 and US 20150037802 A1 which are herein incorporated by reference in their entireties, for descriptions of nanomembranes including NANOBIND™. Each of references 8-10 are herein incorporated by reference in its entirety.

The size cutoff value describes a threshold below which nucleic acid molecules are inefficiently recovered and above which nucleic acid molecules are efficiently recovered. A cutoff size can be defined as the size of nucleic acid whose recovery is half way between the limiting behavior of the low size recovery and the high size recovery. For example, if the low molecular weight nucleic acid molecules (e.g. 10 bp) are recovered with 0% efficiency and high molecular weight nucleic acid molecules (e.g. 50 kbp) are recovered with 100% efficiency, then the cut-off size is the molecular weight that has 50% recovery.

The size cutoff value can also describe a threshold above which nucleic acid molecules are inefficiently recovered and below which nucleic acid molecules are efficiently recovered. A cutoff size can be defined as the size of nucleic acid whose recovery is half way between the limiting behavior of the low size recovery and the high size recovery. For example, if the low molecular weight nucleic acid molecules (e.g. 10 bp) are recovered with 100% efficiency and high molecular weight nucleic acid molecules (e.g. 50 kbp) are recovered with 0% efficiency, then the cut-off size is the molecular weight that has 50% recovery.

As used herein, the term "nucleic acid(s)" or "nucleic acid molecule(s)" are used interchangeably and include "polynucleotide(s)" and "oligonucleotide(s)." The term further includes a polymer of DNA, RNA or cDNA, which can be single-stranded or double stranded, synthesized or obtained (e.g., isolated and/or purified) from natural sources, which can contain natural, non-natural or altered nucleotides, and which can contain a natural, non-natural or altered internucleotide linkage, such as a phosphoramidate linkage or a phosphorothioate linkage, instead of the phosphodiester found between the nucleotides of an unmodified oligonucleotide. The term further includes nucleic acids with other common nucleic acid modifications, including but not limited to fluorophores, quenchers, methylated bases. The nucleic acids to be processed may be described as genomic DNA (gDNA), mitochondrial DNA (mtDNA), plasmid DNA (pDNA), cell-free DNA (cfDNA), circulating nucleic acids, cell-free RNA (cfRNA), microRNA, ribosomal RNA (rRNA), messenger RNA (mRNA), transfer RNA (tRNA), non-coding RNA (ncRNA). High molecular weight DNA is large unfragmented DNA that is typically greater than 20 kb in length, often hundreds of kb in length (up to 100 kb, 200 kb, 300 kb, 500 kb, etc,) and sometimes Mb in length (up to 1 Mb, 2 Mb, 5 Mb+, etc).

As used herein, the term 'desired size range' when used in reference to DNA sizes, is used to describe a set of DNA sizes that are a subset of the DNA sizes contained in the input to a described protocol step, or the size selection process in its entirety. As an example, the input DNA sample is a library preparation product that contains DNA with lengths between 10 bp and 500,000 bp; there are no DNA molecules shorter than 10 bp and none longer than 500,000 bp in the sample. All other sizes are represented with equal number. The desired size range in this example is all DNA molecules above a cutoff size of 300 bp. Thus, the desired size range comprises the subset of input molecules containing DNA with lengths between 300 bp and 500,000 bp; there are no DNA molecules in the desired size range shorter than 300 bp and none longer than 500,000 bp. As another example, the limits are defined in terms of percentage recoveries of DNA greater than or lower than that DNA size. With the same input sample as above: DNA with lengths between 10 bp and 500,000 bp; there are no DNA molecules shorter than 10 bp and none longer than 500,000 bp in the sample. All other sizes are represented with equal number. The desired size range comprises a recovery such that the average recovery for DNA molecules with lengths greater than 300 bp is 90%, and the average recovery for DNA molecules with lengths shorter than 300 bp is 10%. Thus the longer DNA molecules are preferentially recovered.

The nucleic acid-containing sample, such as a DNA-containing sample, comprises nucleic acids, such as DNA molecules, of different sizes (lengths). The method according to the present disclosure allows for the size selection of single stranded as well as of double-stranded nucleic acids. Typically, the nucleic acid molecules are linear, double-stranded DNA molecules. The nucleic acid-containing sample can be of various origins, including biological samples and artificial samples that are obtained during nucleic acid processing. Biological samples can include body fluids such as blood, plasma, serum, urine, feces, sputum, buccal swabs, hair, teeth, bone or other clinical samples such as cultured cells, tissues, and fixed tissues. In some embodiments, the present method is used to purify a body fluid sample containing smaller cfDNA from larger gDNA. In some embodiments, the present method is used to purify small plasmid DNA from larger gDNA in a bacterial culture such as an *E. coli* bacterial culture. In some embodiments, the present method may be used to purify plasmids of different size. In some embodiments, the present method may be used to purify constructs of varying size such as plasmids, cosmids, fosmids, yeast artificial chromosomes, and bacterial artificial chromosomes. According to some embodiments, the nucleic acid-containing sample is a sample of extracted nucleic acid or extracted nucleic acid that has been further processed, e.g. by shearing or by way of an enzymatic reaction. In some embodiments, the nucleic acid sample is a sequencing library preparation. In some embodiments, the present method is used to purify a total RNA sample containing RNA species of different sizes. In some embodiments, the present method is used to isolate a small RNA fraction from a total RNA sample. In some embodiments, the present method is used to isolate larger rRNA or mRNA from a total RNA sample.

According to some embodiments, the nucleic acid-containing sample comprises fragmented nucleic acid, such as DNA, e.g. sheared DNA. According to other embodiments, the nucleic acid-containing sample comprises sheared genomic DNA or sheared cDNA. Thus, according to some embodiments, the nucleic acid-containing sample is a solution resulting from a size shearing procedure such as needle shearing, acoustic shearing, ultrasonic shearing, enzymatic digestion, hydrodynamic shearing, and transposase mediated fragmentation. Such a nucleic acid-containing sample comprises nucleic acid fragments of different sizes. It may be desired to obtain only DNA of a specific size or size range. Said fragmented nucleic acids can be end-repaired to provide nucleic acid fragments having blunt ends. Thus, according to some embodiments, the nucleic acid-containing sample comprises linear, blunt-ended DNA fragments of different sizes.

According to certain embodiments, the nucleic acid-containing sample is obtained after an enzymatic reaction. Exemplary enzymatic reactions that provide nucleic acid-containing samples that can be processed using the method of the disclosure includes but are not limited to polymerase chain reaction, ligation reactions, damage repair, end repair, poly-A tailing, reverse transcription, nuclease digestion, transposition, methylation, transcription, loop-mediated isothermal amplification, body labeling, and end labeling. Thus, according to some embodiments, the nucleic acid-containing sample is a solution resulting from an amplification procedure and comprises amplification products, e.g. PCR products. According to certain embodiments, the nucleic acid-containing sample is an adapter ligation sample that is obtained as a result of an adapter ligation step. In such enzymatic reactions, it may be desirous to purify the desired enzymatic reaction products from unused reactants, enzymes, reaction side products, and reaction buffers. Enzymatic reaction products can often be differentiated from reaction side products and unused reactants by size. In some embodiments, larger PCR amplification products are purified from smaller PCR primers, dNTPs, and primer dimers. In other embodiments, larger ligation products, for example gDNA-adapters, are purified from smaller pre-ligation inputs, for example unligated adapters.

In some embodiments, the enzymatic reaction is one step in a series of steps in a library preparation for sequencing. Typical library preparations for sequencing reactions include adapter ligation. According to a typical embodiment, adapters are modified or unmodified nucleic acid oligomers. Adapters can also be complexed with enzymes, other proteins or other non-nucleic acid molecules including, but not limited to, biotins. Adapters can be single stranded, double stranded, contain hairpins, and have blunt ends or one or more nucleotides overhanging at the 5' or 3' end. Single stranded adapters can be ligated to the 5' or 3' end or both 5' and 3' ends of a sample nucleic acid. Double stranded adapters, including those with hairpins can be ligated either by blunt end or sticky end ligation.

According to certain embodiments, hairpin adapters can be attached to sample DNA molecules utilizing polymerase-facilitated primer extension.

According to certain embodiments, the nucleic acid-containing sample is obtained during the preparation of a sequencing library, in particular during preparation of a third generation sequencing library. According to a typical embodiment, the nucleic acid molecules in the sample have nucleic acid adapters (such as defined herein) ligated onto their 5' or 3' or both 3' and 5' ends. Thus, the sample may include unligated sample nucleic acid molecules, ligated sample nucleic acid molecules, unligated adapters, ligated adapter dimers, trimers and other combinations of adapter, plus other reagents including, but not limited to buffer species and enzymes. The method according to the present disclosure allows for size selective purification of double-stranded or single stranded nucleic acid, such as DNA molecules, that are flanked by 5' and/or 3' by adapters, thereby efficiently removing respective contaminants. After ligation, the DNA molecules are typically longer than the unligated adapters, therefore enabling purification based on size.

According to certain embodiments, the method according to the present disclosure is used after digestion of unprotected nucleic acid molecules to leave protected nucleic acid molecules. The digestions include but are not limited to ExonucleaseIII, ExonucleaseVII, Lambda Exonuclease, Exonuclease I, Exonuclease VIII, T5 Exonuclease, T7 Exonuclease, T7 Exonuclease I.

According to certain embodiments, the method is used after completion of a library (final library molecules) to select only library molecules of a specific size or size range. In other embodiments, the method is used on nucleic acid starting materials, such that only nucleic acid molecules of a specific size or size range are input into the library preparation. In other embodiments, size selection is performed after an amplification step in library preparation. In other embodiments, size selection is performed after, but not limited to, a poly-A tailing, end-repair, nuclease digestion, damage repair, adapter ligation and/or transposition steps during library preparation.

Chaotropic agents or salts as used herein refer to compounds that change or disrupt the secondary structure, tertiary structure, and/or quaternary structure of proteins, nucleic acids, and protein-nucleic acid complexes while the primary structure remains intact. In solution, under chaotropic conditions, the intramolecular interactions of biological molecules, such as proteins, protein-nucleic acid complexes, and nucleic acids, are disrupted since chaotropic compounds interfere with stabilizing intramolecular interactions in biological molecules, for example hydrogen bonds, van der Waals forces, and hydrophobic effects. Chaotropic compounds usually have large-volume ions that, owing to their size, can interfere with intermolecular interactions and reduce the polarity of a solvent, thereby disrupting intermolecular and intramolecular hydrogen bonds. Consequently, many proteins precipitate; however, the helical structure of double stranded nucleic acid segments is maintained. By adding chaotropic compounds to reaction solutions, proteins can be precipitated while nucleic acids remain in solution. Under chaotropic conditions, the binding of nucleic acids to silicon dioxide-based matrices is greatly favored. Chaotropic salts include, for example, guanidinium salt solutions (e.g., 6 mol/l such as guanidinium chloride) and high concentration lithium salts (e.g., 4.5 mol/l lithium perchlorate). Other examples include guanidinium thiocyanate, guanidinium isothiocyanate and sodium iodide.

The present disclosure is directed to a method for isolating nucleic acids in a desired size range comprising: a) combining a nucleic acid-containing sample with a binding buffer to provide a binding mixture, b) contacting the binding mixture with a nanomembrane, wherein the nanomembrane binds nucleic acids in the binding mixture with specific sizes, c) optionally washing the bound nucleic acid and nanomembrane with a wash buffer to further remove impurities or facilitate size selection and d) separating or eluting specific sizes of the bound nucleic acid from the nanomembrane.

In some embodiments, obtaining a desired nucleic acid size range is facilitated by at least one binding condition, wherein at least one binding condition is selected from i) pH, ii) salt concentration, iii) presence or absence of chaotropic salts, iv) presence or absence of monovalent and/or divalent salts, v) alcohol type and concentration, vi) molecular crowder concentration, vii) species of molecular crowder, viii) binding time, ix) temperature during binding x) the presence or absence of denaturing agents xi) the presence of absence of other molecular species xii) buffer volume xiii) motion of tube during binding, for example vortexing, centrifugation, shaking, rotating xiv) size of nanomembrane xv) shape of nanomembrane xvi) 3D conformation of nanomembrane xvii) number of nanomembranes and xviii) combinations thereof.

Small Size Select

Typically, small size select nanomembrane nucleic acid purification follows the sequence of: 1) the sample containing nucleic acids to be purified plus contaminants to be removed is aliquoted to, e.g., a microcentrifuge tube; 2) a binding buffer is added to the sample, followed by e.g., alcohol and a nanomembrane; these components are mixed; and this mixture is incubated, during which time the nucleic acids bind to the nanomembrane; 3) the binding buffer mix with or without alcohol is removed from the microcentrifuge tube, leaving the nucleic acid bound to the nanomembrane in the tube; 4) a wash buffer, usually containing alcohol, water, buffer and salt is added to the microcentrifuge tube and the tube is inverted 5-10 times; 5) the wash buffer is removed from the tube; 6) elution buffer is added to the tube such that the nanomembrane is completely submerged; at this step, the nucleic acid becomes detached from the nanomembrane and is in solution in the elution buffer; 7) the elution buffer containing the nucleic acid is transferred to a separate tube, which thus contains the final, purified nucleic acid.

In some embodiments the protocol described herein is performed by an automated robot, for example KingFisher (ThermoFisher) or Maxwell® and Maxprep™ (Promega).

Binding to Nanomembrane

In some embodiments, the present method is directed to isolating nucleic acids having a size at or above a cut-off value to obtain isolated nucleic acids of a desired size range. In certain embodiments, the desired size range of nucleic acids obtained using the instant method is greater than or equal to a cutoff that can vary between 10 base pairs (bp) (for double stranded nucleic acids) or 10 nucleotides (nt) (for single stranded nucleic acids) to greater than or equal to about 30000 bp or 30000 nt e.g., >10 bp (or nt), >25 bp (or nt), >50 bp (or nt), >100 bp (or nt), >150 bp (or nt), >200 bp (or nt), >250 bp (or nt), >300 bp (or nt), >350 bp (or nt), >400 bp or (nt), >500 bp or (nt), >600 bp or (nt), >700 bp or (nt), >800 bp or (nt), >900 bp or (nt), >1000 bp or (nt), >2500 bp or (nt), >3000 bp or (nt), >4000 bp or (nt), >5000 bp or (nt), >6000 bp or (nt), >7000 bp or (nt), >8000 bp or (nt), >9000 bp or (nt), >10000 bp or (nt), >20000 bp or (nt), >30000 bp or (nt) (also referred to herein as "Small Size Select").

As used herein, the term "binding conditions" refer to those conditions as described herein that affect the sizing cutoff. Binding conditions may be affected by components of the binding buffer, binding time, binding temperature, size, shape and conformation of the nanomembranes, etc.

In certain embodiments, the binding buffer may be designed to facilitate decreasing the sizing cutoff. In other embodiments, the binding buffer may be designed to facilitate increasing the sizing cutoff. In certain embodiments, the sizing cutoff can be tailored by selectively denaturing double stranded nucleic acids of a specific size or range. In some embodiments, this may be achieved by adjusting the binding buffers to favor binding of double stranded nucleic acids over single stranded nucleic acids and then by selectively denaturing shorter nucleic acids versus longer nucleic acids. In this manner, shorter nucleic acids may be prevented from binding and removed from the sample. In some embodiments, this may be achieved by adjusting the pH of the binding buffer. For example, more alkaline solutions with higher pHs destabilize the secondary structure of nucleic acids. In certain embodiments, the pH of the binding buffer may be adjusted to alter the fraction of double- and single-stranded nucleic acids. Single stranded and double stranded nucleic acids have different propensities to bind to the nanomembrane in a size dependent manner. Thus, in some embodiments, changing the pH changes the cut-off of the returned nucleic acids. In other embodiments, the pH of the binding buffer may be used to affect the surface charge of the nanomembrane to impart preference to single stranded versus double stranded and shorter versus longer nucleic acids. In these embodiments, the pH can be varied in the range of 5-13, for example pH=5, 5.5, 6, 6.5, 7, 7.5, 8, 8.5, 9, 9.5, 10, 10.5, 11, 11.5, 12, 12.5, or 13.

In other embodiments, denaturing agents may be added to the binding buffer to selectively denature nucleic acids of a specific size or range. Denaturing agents disrupt nucleic acid secondary structure in a size-dependent manner; shorter nucleic acids have lower melting temperatures and can be denatured at lower denaturant concentrations. Thus, by preferentially melting shorter nucleic acids, the binding cut-off is shifted to longer nucleic acid lengths. For example, betaine with concentration between 0.1 and 5M may be used as a denaturing agent.

In certain embodiments, the sizing cutoff can be tailored by selectively adjusting the solubility of nucleic acids of a specific size or range. In some embodiments, this may be achieved by adjusting the salt concentration of the binding buffer. This can include the presence or absence of chaotropic salts, the presence or absence of monovalent (e.g., sodium chloride, potassium chloride) and/or divalent salts (e.g. magnesium chloride) in the binding buffer. Higher chaotropic, monovalent and divalent salt concentrations reduce the solubility of all nucleic acids and can decrease sizing cutoffs. The concentration of chaotropic salts, for example GuHCl can be varied between 0.001M and 8M. The concentration of monovalent salts, for example NaCl can be varied between 0.001M and 6M. The concentration of divalent salts, for example $MgCl_2$, can be varied between 0.01 mM and 1000 mM.

In certain embodiments, the solubility of nucleic acids and, hence, the sizing cutoff can be tuned by adjusting the concentration of alcohol in the binding buffer. Suitable alcohols include but are not limited to methanol, ethanol, propanol, isopropanol and butanol. Higher alcohol concentration reduces the solubility of the nucleic acids and can decrease sizing cutoffs. The alcohol concentrations can be varied between about 0% and about 99%, for example 0%, 5%, 10%, 15%, 20%, 25%, 30%, 35%, 40%, 45%, 50%, 55%, 60%, 65%, 70%, 75%, 80%, 85%, 90%, 95%, 99%.

In certain embodiments the DNA is bound in a binding solution containing no alcohol.

In certain embodiments, the solubility of nucleic acids and, hence, the sizing cutoff can be tuned by changing the volume of the binding buffer. Higher binding volumes result in lower nucleic acid concentrations under binding conditions. Shorter nucleic acids bind less well at lower concentrations than longer nucleic acid molecules; thus increasing the volume of binding buffer shifts the binding cut-off to longer nucleic acid molecules. The volume of binding buffers can be varied from 0.1× in the input sample volume to 10× in the input sample volume. The nucleic acid concentrations can be varied from approaching zero concentration to up to 500 ng/µl.

In certain embodiments, the sizing cutoff can be tuned by the addition of molecular crowders of varying concentration and/or composition, including but not limited to, polyethylene glycol, Ficoll, BSA, linear acrylamide, polyvinylpyrrolidone and glycogen. Crowders tend to lower the free energy of aggregated or adsorbed molecules with respect to those fully in solution compared with solutions without crowders. Thus, crowders drive binding of DNA to the nanomembrane. The effects of crowders are well known to be size-dependent[11], with molecules of similar size to the crowders experiencing the largest effects. Crowders therefore shift the binding cut-off of nucleic acid molecules. Polyethylene glycol concentration can be varied between about 0% and about 40%. Polyvinylpyrrolidone concentration can be varied between about 0% and about 40%. Ficoll concentration can be varied between about 0% and about 20%. Linear acrylamide and glycogen can be varied between about 0 and about 500 ng/µl. BSA can be varied between about 0 and about 10 mg/ml.

In certain embodiments, polyamines such as spermine, spermidine, cadaverine or putrescine can be used to tune the sizing cutoff. Spermine and spermidine are known to induce precipitation of nucleic acids in a length dependent manner[12]. Thus, these polyamines can be used to adjust the size dependence of the precipitation and binding to a nanomembrane.

In certain embodiments, surfactants can be used to change the surface tension of the binding solution and therefore the solubility of nucleic acids in a size dependent manner. Surfactants include, but are not limited to TWEEN 20, sodium dodecyl sulfate, Triton-X100, Triton-X114, NP40, cetrimonium bromide, dodecyltrimethylammonium bromide. All can be varied between 0% and 10%. Therefore these surfactants can be used to adjust the size dependence of the precipitation and binding to a nanomembrane.

In certain embodiments, the sizing cutoff can be tuned by adjusting the binding time. Shorter nucleic acid molecules take longer to come out of solution and adsorb to nanomembranes. Thus, longer binding times shift the binding cut-offs to shorter nucleic acid molecules. Binding times can be adjusted between 1 minute and 5 days.

In certain embodiments, sizing cutoff can be tuned by adjusting the binding temperature. Higher temperatures melt nucleic acid secondary structure in a size-dependent manner, shorter nucleic acids melting at lower temperatures than longer nucleic acids. Thus, by preferentially melting shorter nucleic acids, the binding cut-off is shifted to longer nucleic acid lengths. In other embodiments, temperature may be used to selectively adjust the solubility of nucleic acids of a specific size or range. The temperature of binding can be adjusted between about −20° C. to about 70° C.

In certain embodiments, the binding conditions encompass motion during binding including but not limited to, vortexing, shaking, inverting, centrifugation, rotating, tapping. In order to bind to the nanomembrane, DNA has to pass close enough to the surface of the nanomembrane to encounter the attractive forces described herein. Since larger DNA molecules sweep through more of the solution per molecule there is a larger probability of them encountering a nanomembrane than a small DNA molecule. This can be changed by using such motions, for example faster shaking or vortexing, as to cause the nanomembrane to move about in solution more rapidly thus increasing the probability that it will encounter a short DNA molecule and bind it, whilst not significantly changing the high binding probability of the larger DNA molecules.

In certain embodiments, the binding conditions encompass the size and shape and conformation of the nanomembrane. Shapes used include, but are not limited to, circles, squares, stars, crescents, rings. Conformations include, but are not limited to, tubes, spheres, cubes and scrunched. Different conformations of the nanomembrane can be used to change the way in which fluid flows across the surface. For example, a scrunched conformation reduces the expected flow across parts of the surface that are not directly facing out into the solution. Since smaller DNA molecules are less likely to encounter a nanomembrane surface with lower flow across the surface they are less likely to be bound to scrunched nanomembrane.

In certain embodiments, the binding conditions encompass the number of nanomembranes. The number of nanomembranes can be, but is not limited to 1, 2, 3, 4, 5, 6, 7, 8, 9, 10, 20, 30, 40, 50, 60, 70, 80, 90, 100, 1000, 10000, 100000, $1\times10^6$, $1\times10^7$, $1\times10^8$, $1\times10^9$. In order to bind to the nanomembrane, DNA has to pass close enough to the surface of the nanomembrane to encounter the attractive forces described herein. Since larger DNA molecules sweep through more of the solution per molecule there is a larger probability of them encountering a nanomembrane than a small DNA molecule. This can be changed by increasing the number of nanomembranes as this will increase the encounter probability and binding of short DNA molecules, whilst not significantly changing the high binding probability of the larger DNA molecules.

Any combination of the foregoing conditions described herein can be used to change size selection parameters of the present method.

In certain embodiments, the binding buffers are chosen such that both nucleic acids and proteins bind to the nanomembrane and can therefore be co-purified from the rest of the sample. In other embodiments, the binding buffers are chosen such that proteins that are bound to nucleic acids in the sample will not be disrupted and can be co-purified by binding nucleic acids to the nanomembrane.

Washing and Elution

In some embodiments, the bound nucleic acids according to the small size selection method are washed. Here, one or more washing steps can be performed. Typically, this step is performed to efficiently remove unbound components and impurities such as e.g. nucleotides and enzymes from previous reactions. This is particularly suitable if the nucleic acid containing sample was obtained during the preparation of a sequencing library. In addition, washing steps can be used to remove nucleic acid size fractions, leaving behind the desired size fraction. Furthermore, washing steps are also suitable to remove traces of a chaotropic salt or other salt used during binding, if it could interfere with the intended downstream process.

As used herein, the term "washing conditions" refer to those conditions as described herein that affect the sizing cutoff. Washing conditions may be affected by components of the washing buffer, washing time, washing temperature, size, shape and conformation of the nanomembranes, etc.

According to some embodiments, the solution used for washing comprises at least one salt and/or at least one alcohol. Salts that can be used in the washing solutions include but are not limited to guanidinium hydrochloride, guanidinium thiocyanate, guanidinium isothiocyanate, sodium iodide, sodium chloride, potassium chloride, magnesium chloride, calcium chloride, sodium acetate, potassium acetate or other salts. As alcohol, short chained branched or unbranched alcohols with typically one to 5 carbon atoms can be used for washing. Also, mixtures of alcohols can be used in the washing solution. Suitable alcohols include but are not limited to methanol, ethanol, propanol, isopropanol and butanol. Typically, isopropyl alcohol and/or ethanol are used in the washing solution.

In some embodiments, the method further comprises washing the nanomembrane to remove nucleic acids that are not of the desired size range. In certain embodiments, the removal of specific nucleic acid sizes by washing is facilitated by at least one condition of the wash solution selected from i) pH, ii) salt concentration, ii) presence or absence of chaotropic salts, iii) presence or absence of monovalent and/or divalent salts, iv) alcohol concentration, v) molecular crowder concentration, vi) species of molecular crowder, vii) washing time, viii) temperature during washing ix) the presence or absence of denaturing agents x) other additive molecules such as spermine, spermidine, surfactants xi) wash solution volume xii) wash solution temperature and xiii) combinations thereof.

In certain embodiments, the pH of the wash solution may be adjusted to alter the fraction of double- and single-stranded nucleic acids. Single stranded and double stranded nucleic acids have different propensities to bind to the nanomembrane in a size dependent manner. Thus, in some embodiments, changing the pH changes the cut-off of the nucleic acid molecules that are washed away from the nanomembrane. In other embodiments, the pH of the wash solution may be used to affect the surface charge of the nanomembrane to impart preference of shorter versus longer nucleic acids. In these embodiments, the pH can be varied in the range of 5-13, for example pH=5, 5.5, 6, 6.5, 7, 7.5, 8, 8.5, 9, 9.5, 10, 10.5, 11, 11.5, 12, 12.5, or 13

In certain embodiments, the solubility of nucleic acids and, hence, the sizing cutoff can be tuned by adjusting the concentration of alcohol in the wash solution. Suitable alcohols include but are not limited to methanol, ethanol, propanol, isopropanol and butanol. Higher alcohol concentration reduces the solubility of the nucleic acids and can decrease sizing cutoffs. The alcohol concentrations can be varied between about 0% and about 99%, for example 0%, 5%, 10%, 15%, 20%, 25%, 30%, 35%, 40%, 45%, 50%, 55%, 60%, 65%, 70%, 75%, 80%, 85%, 90%, 95%, 99%.

In certain embodiments, the solubility of nucleic acids and, hence, the sizing cutoff can be tuned by adjusting the concentration of salt in the wash solution. Suitable salts include but are not limited to guanidinium hydrochloride, guanidinium thiocyanate, guanidinium isothiocyanate sodium iodide, sodium chloride, potassium chloride, magnesium chloride, calcium chloride, sodium acetate, potassium. Higher salt concentration reduces the solubility of the nucleic acids and can decrease sizing cutoffs. The salt, for example but not limited to sodium chloride, concentration can be varied between about 0 mM and about 5000 mM, for example 0 mM, 5 mM, 10 mM, 15 mM, 20 mM, 25 mM, 30 mM, 40 mM, 50 mM, 100 mM, 150 mM, 200 mM, 250 mM, 300 mM, 400 mM, 500 mM, 600 mM, 700 mM, 800 mM, 900 mM, 1000 mM, 1500 mM, 2000 mM, 2500 mM, 3000 mM, 3500 mM, 4000 mM, 4500 mM, 5000 mM.

In some embodiments, the method contains no alcohol in the wash.

In some embodiments, the method contains polyamine in the wash for example spermine or spermidine. Spermine and spermidine are known to induce precipitation of nucleic acids in a length dependent manner[12]. Thus, these polyamines can be used to adjust the size dependence of washing of the nanomembrane.

In certain embodiments, the solubility of nucleic acids and, hence, the sizing cutoff can be tuned by adjusting the concentration of molecular crowders in the wash solution. Suitable molecular crowders include but are not limited to polyethylene glycol, Ficoll, BSA, linear acrylamide, polyvinylpyrrolidone and glycogen. Higher molecular crowder concentration reduces the solubility of the nucleic acids and can decrease sizing cutoffs. The molecular crowder concentrations can be varied between about 0% and about 40%, for example 0%, 1%, 1.5%, 2%, 2.5%, 3%, 3.5%, 4%, 4.5%, 5%, 10%, 15%, 20%, 25%, 30%, 35%, 40%.

In certain embodiments, the solubility of nucleic acids and, hence, the sizing cutoff can be tuned by adjusting the concentration of surfactants in the wash. Surfactants include, but are not limited to TWEEN 20, sodium dodecyl sulfate, Triton-X100, Triton-X114, NP40, cetrimonium bromide, dodecyltrimethylammonium bromide. All can be varied between 0% and 10%.

Any elution solution can be used which effects desorption of the bound nucleic acid from the nanomembrane. Classical elution solutions known to effectively elute nucleic acid from a silica surface include but are not limited to water, elution buffers such as TE-buffer, low EDTA TE buffers, and low-salt solutions which have a salt content of 150 mM or less to about 10 mM or are salt-free.

In some embodiments, one or more elution steps are performed in order to elute the purified size selected nucleic acid. The eluate, including nucleic acid and buffers, are then typically removed from the tube containing the nanomembrane to be used in a downstream application. In some embodiments, however, the elution buffer contains reagents for downstream manipulation of the purified nucleic acid and/or proteins. The downstream reaction is then initiated and completed with the nanomembrane still present in the solution. At completion of the reaction, binding buffers are added to the e.g., microcentrifuge tube and the nucleic acids are re-bound to the same nanomembrane that remains in the e.g., tube.

In some embodiments, the method further comprises specifically eluting nucleic acids that are of the desired size range and leaving nucleic acids not of the desired size range bound to the nanomembrane. In certain embodiments, the cut-off value is facilitated by at least one condition of the elution solution selected from i) pH, ii) salt concentration, ii) presence or absence of chaotropic salts, iii) presence or absence of monovalent and/or divalent salts, v) molecular crowder concentration, vi) species of molecular crowder, vii) eluting time, viii) temperature during elution ix) the presence or absence of denaturing agents x) other additive molecules such as spermine, spermidine, surfactants xi) elution solution volume xii) elution solution temperature and xiii) combinations thereof.

In other embodiments, no washing of the nanomembrane is performed. In some embodiments, the nanomembrane disk is removed from the binding buffer and nucleic acids are eluted without washing. In other embodiments, the nanomembrane disk is removed from the binding buffer and used without eluting the nucleic acid.

Large Size Select

In certain embodiments, the nanomembranes of the present disclosure, such as NANOBIND™, are capable of selecting large nucleic acid fragments for removal from a nucleic acid-containing sample to achieve a tunable cutoff of large reaction products (ranging from 200 bp (or nt) to 100 kb). In certain embodiments, the desired size range of nucleic acids obtained using the instant method is greater than or equal to about 200 base pairs (bp) (for double stranded nucleic acids) or 200 nucleotides (nt) (for single stranded nucleic acids) or greater than or equal to about 500 bp or 500 nt e.g., ≥1000 bp (or nt), ≥2000 bp (or nt), ≥3000 bp (or nt), ≥5000 bp (or nt), ≥7000 bp (or nt), ≥8000 bp (or nt), ≥9000 bp (or nt), ≥10,000 bp or (nt), ≥20,000 bp or (nt), ≥30,000 bp or (nt), ≥40,000 bp or nt, ≥50,000 bp or (nt), ≥60,000 bp or (nt), ≥70,000 bp or (nt), ≥80,000 bp or (nt), ≥90,000 bp or (nt), ≥100,000 bp (nt) (nt) (also referred to herein as "Large Size Select").

In some embodiments, Large Size Select processes incorporate molecular crowders[13]. As is well known in the art, "molecular crowders" are compounds that can impart size-based binding due to excluded volume effects. Suitable molecular crowders for use with the present method include, but are not limited to, polyvinyl pyrrolidinone (PVP), such as PVP(Mw10,000), PVP(Mw29,000), PVP(Mw40,000), PVP(Mw55,000), PVP(Mw360,000), PVP(Mw1,300,000), polyethylene glycol (PEG), such as PEG 1000, PEG 2000, PEG 3000, PEG 4000, PEG 5000, PEG 6000, PEG 7000, PEG 8000, PEG 9000, PEG 10,000, PEG 11,000, PEG 12,000, PEG 13,000, PEG 14,000, PEG 15,000, PEG 16,000, PEG 17,000, PEG 18,000, PEG 19,000 and PEG 20,000, glycogen, ficoll, BSA, maltodextrin, linear acrylamide. In other embodiments, a mixture of molecular crowders may be used. Reference 13 is hereby incorporated by reference in its entirety. The concentration of the crowders can be adjusted between about 0% and about 40%.

In some embodiments, a size selecting precipitation and pelleting step is performed prior to a nanomembrane purification method similar to that outlined herein. In some embodiments, a size selecting precipitation and pelleting step is performed after a nanomembrane purification method similar to described herein. In some embodiments, the method for large size selection occurs concurrently with the nanomembrane purification method.

In some embodiments, a separate size selecting precipitation step is used. This method may be exemplified as follows: 1) a precipitation buffer, containing, but not limited to, water, buffer, salt, and PVP(Mw360,000) is added to the nucleic acid-containing sample; 2) the sample-buffer is centrifuged at 8000 g for 30 minutes at room temperature, during this step, the nucleic acid will pellet at the bottom of the tube; 3) the supernatant is removed from the tube; 4) 70% alcohol is added to the tube and centrifuged at 8000 g for 2 minutes at room temperature; 5) the 70% alcohol supernatant is removed from the tube and the nucleic acid pellet is re-suspended in elution buffer.

In some embodiments, large size selection occurs concurrently with the nanomembrane purification method, which typically follows the sequence of: 1) the sample containing nucleic acids to be purified plus contaminants to be removed is aliquoted to e.g., a microcentrifuge tube; 2) a binding buffer is added to the sample, followed by, but not limited to, alcohol and a nanomembrane; these components are mixed; this mixture is incubated, during which time the nucleic acid binds to the nanomembrane; 3) the binding buffer/alcohol mix is removed from the microcentrifuge tube, leaving the nucleic acid bound to the nanomembrane in the tube; 4) a wash buffer, containing, but not limited to, alcohol, water, buffer and salt is added to the microcentrifuge tube and the tube is inverted 5-10 times; 5) the wash buffer is removed from the tube; 6) elution buffer is added to the tube such that the nanomembrane is completely submerged; at this step, the nucleic acid becomes detached from the nanomembrane and is in solution in the elution buffer; 7) the elution buffer containing the nucleic acid is transferred to e.g., a separate tube, which thus contains the final, purified nucleic acid.

In certain embodiments, the large size select process is tuned by optimizing the amount (for example, 0.1%-40%) and/or type (for example, PVP having a molecular weight from 10,000 to 1,300,000) of molecular crowder in the precipitation step described herein, or during the binding step described herein. In certain embodiments, the large size select process is tuned by optimizing the precipitation or binding time (2-60 minutes), temperature (4-50° C.) and or combinations thereof.

In some embodiments, the cut-off value of the large size select process is tuned by at least one of the following binding conditions: i) pH, ii) salt concentration, iii) presence or absence of chaotropic salts, iv) presence or absence of monovalent and/or divalent salts, v) alcohol type and concentration, vi) molecular crowder concentration and molecular weight, vii) species of molecular crowder, viii) precipitation/binding time, ix) temperature during precipitation/binding x) the presence or absence of denaturing agents xi) the presence of absence of other molecular species xii) buffer volume xiii) motion of tube during binding, for example vortexing, centrifugation, shaking, rotating xiv) size of nanomembrane xv) shape of nanomembrane xvi) 3D conformation of nanomembrane and xvii) combinations thereof.

In certain embodiments, molecular crowders are used to tune cut-off values of size selection. Molecular crowders change solution free energies of molecular species in a way that is highly dependent on the concentration and size of both the molecular crowder and the molecular species in question[11,13]. This makes it possible to tune the solubility of nucleic acids using molecular crowders in a way that is highly dependent on the size of the nucleic acid. For example, in certain embodiments, a higher percentage of molecular crowder, such as PVP, increases excluded volume effects such that smaller molecules are increasingly brought out of solution. In another example, higher molecular weight molecular crowders, e.g., PVP 360,000, may be used to shift the molecular crowding effect to larger molecules and preferentially drive the precipitation and aggregation of larger sized nucleic acids.

High Pass, Low Pass, and Band Pass Purifications

In certain embodiments, the present method can be used to recover a desired size range of nucleic acids that are larger than the sizing cutoff (i.e. high-pass). High-pass methods are described herein, for example.

In other embodiments, the present method can be used to recover nucleic acids that are smaller than the sizing cutoff (i.e. low-pass). The low-pass purification typically follows the sequence of: 1) the sample containing nucleic acids to be purified plus contaminants to be removed is aliquoted to e.g., a microcentrifuge tube; 2) a binding buffer is added to the sample, followed by the addition of e.g., alcohol and a nanomembrane; these components are mixed; this mixture is incubated, during which time nucleic acid above a cutoff length binds to the nanomembrane; 3) the binding buffer/alcohol mix is removed from the microcentrifuge tube; this binding buffer/binding mixture contains small nucleic acids below the cutoff length; 4) the removed binding buffer/alcohol/nucleic acid is adjusted by adding for example, but not limited to, more alcohol; 5) a second nanomembrane is added to this solution followed by incubation, during which time the remaining nucleic acid binds to the nanomembrane; 6) the second binding solution is removed from the microcentrifuge tube; 7) a wash buffer, containing e.g., alcohol, water, buffer and salt is added to the microcentrifuge tube and the tube is inverted e.g., 5-10 times; 8) the wash buffer is removed from the tube; 9) elution buffer is added to the tube such that the nanomembrane is completely submerged; at this step, the nucleic acid becomes detached from the nanomembrane and is in solution in the elution buffer; 10) the elution buffer containing the nucleic acid with sizes below the cutoff size is transferred to e.g., a separate tube, which contains the final, purified nucleic acid.

In some embodiments the low-pass method can be achieved by following a method similar to the high pass methods described herein but with high pH binding buffer.

In certain embodiments, the sequential application of the present method can be used to allow a band of DNA sizes between a minimum and a maximum to be selected (i.e. band-pass). Thus, binding conditions are used such that nucleic acid molecules with size above a cut-off $C_1$ are bound to the nanomembrane, leaving those nucleic acid molecules smaller than $C_1$ in solution in the binding buffer. The binding buffer is then transferred to another microcentrifuge tube, for example, and additional buffer with, for example, higher alcohol content is added to the original buffer. A second nanomembrane is then added. The buffer conditions are such that nucleic acid molecules with a size above a cut-off $C_2$ bind to the nanomembrane. The method then continues by washing and eluting as described elsewhere in this disclosure. The final recovered nucleic acid molecules are selected to be in a band between a minimum of $C_2$ and a maximum of $C_1$.

Figure 2:
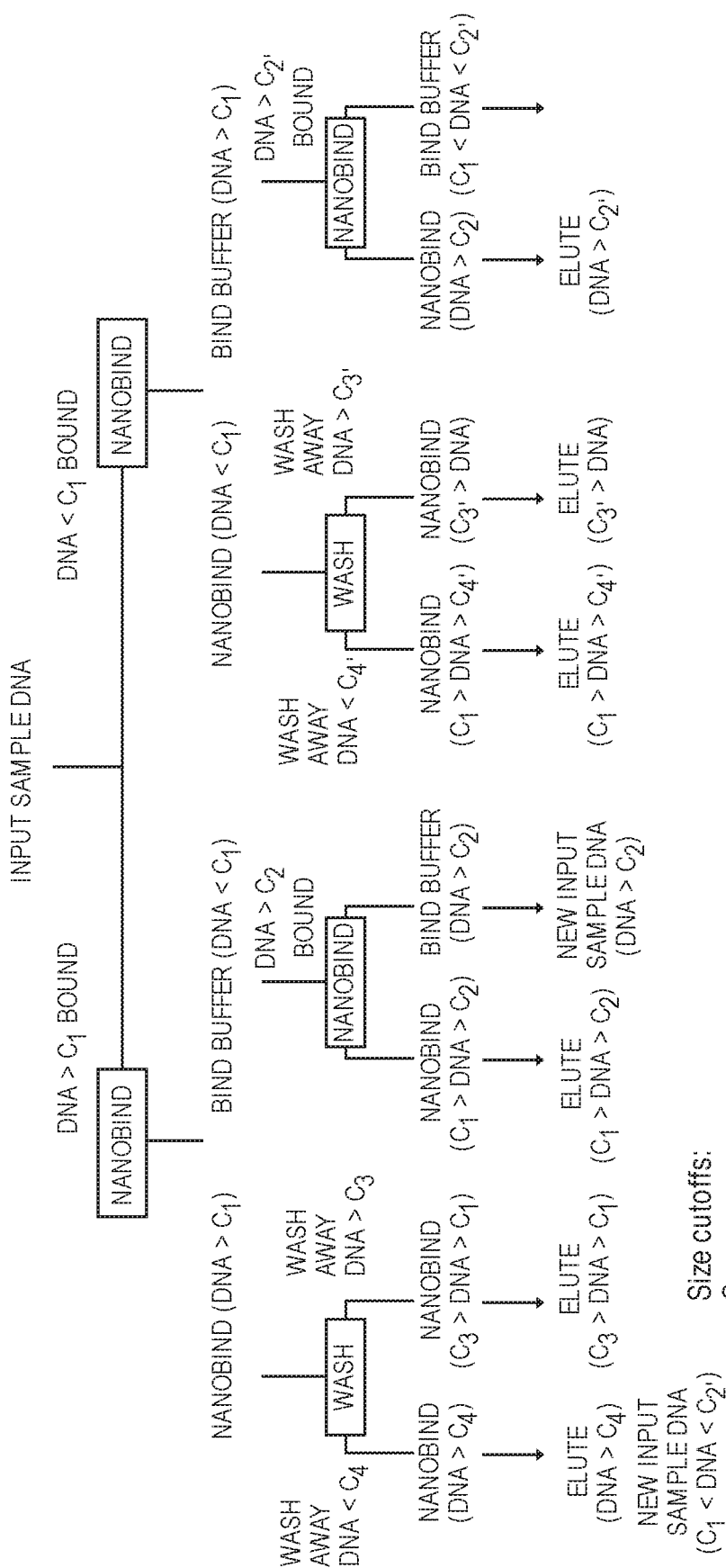
FIG. 2 depicts different processes to achieve size selection purification using a thermoplastic silica nanomaterial. The "Input Sample DNA" can be any typical DNA-containing solution, for example the result of a sequencing library preparation. "NANOBIND" in the flow chart represents the process defined herein: 1)-3), resulting in a NANOBIND with DNA bound to it (size range of DNA bound given in parentheses after Nanobind) and binding buffer, which may contain additional alcohol (size range of DNA in binding buffer given in parentheses after BIND BUFFER). Wash steps are represented by "WASH" and are accompanied by the ranges of DNA sizes that are washed away from the NANOBIND. The Size ranges of DNA that are bound to the NANOBIND, and subsequent elute contents are shown at the bottom of the flow chart.

In certain embodiments, DNA is recovered in a desired size range by following protocols in order as depicted in FIG. 2. For example, the example provided herein follows the path ending with Elute ($C_1$>DNA>$C_2$) where $C_2$=0. The example provided herein follows the path ending with Elute ($C_1$>DNA>$C_2$) where $C_1$>$C_2$>0.

In certain embodiments, the purification can proceed to obtain a desired DNA size range with a lower limit of $C_1$ and an upper limit of $C_3$. This method is depicted in FIG. 2, ending in Elute ($C_3$>DNA>$C_1$). This purification typically follows the sequence of: 1) the sample containing nucleic acids to be purified plus contaminants to be removed is aliquoted to e.g., a microcentrifuge tube; 2) a binding buffer is added to the sample, followed by the addition of e.g., alcohol and a nanomembrane; these components are mixed; this mixture is incubated, during which time nucleic acid above a cutoff length, $C_1$, binds to the nanomembrane; 3) the binding buffer/alcohol mix is removed from the microcentrifuge tube; 4) a wash buffer, containing e.g., alcohol, water, buffer and salt is added to the microcentrifuge tube and the tube is inverted e.g., 5-10 times, nucleic acids above a size cutoff, $C_3$, become unbound from the nanomembrane and are in solution in the wash buffer; 5) the wash buffer, containing nucleic acids above a size cutoff, $C_3$, is removed from the tube; 6) elution buffer is added to the tube such that the nanomembrane is completely submerged; at this step, the bound nucleic acid becomes detached from the nanomembrane and is in solution in the elution buffer; 7) the elution buffer containing the nucleic acid molecules with sizes greater than the lower cutoff, $C_1$, and smaller than the high cutoff, $C_3$, is transferred to e.g., a separate tube, which contains the final, purified nucleic acid.

In certain embodiments, the purification can proceed such that both the high-pass fractions and the low-pass fractions are recovered. The low-pass method is followed as described herein. During step 3) the nanomembrane left in the microcentrifuge has nucleic acids with sizes above the cut-off bound to it. Parallel to the low-pass method described herein, this nanomembrane is washed and eluted as described elsewhere in this disclosure. The result is typically two eluates, one containing nucleic acid above the cutoff and one below.

Sequencing Libraries

The method according to the present disclosure is particularly suitable for size selection in the context of a sequencing library, e.g., a 3rd generation sequencing library. A sequencing library which is suitable for 3rd generation sequencing, for example, can be prepared using methods known in the art. Library preparation for such long-read sequencing technologies, e.g., sequences of tens of thousands or even hundreds of thousands of base pairs, follows a similar workflow. Typically, high MW (50 kb-Mb+) DNA is isolated. Next, the DNA is typically prepared for sequencing using various enzymatic reactions such as ligation, end repair, and labeling. During enzymatic processing, small size selection reaction purification as described in this submission may be performed to remove small background molecules (e.g. those with a tunable cut off value between 50 nt or bp and 30000 nt or bp) such as primer dimers, enzymes, and adapter oligos from the library products.

In certain embodiments, the preparation of a sequencing library often involves the generation of a plurality of double-stranded, linear DNA fragments from a nucleic acid containing sample. For example, DNA, such a genomic DNA or cDNA, can be fragmented by shearing, such as sonication, hydro-shearing, ultrasound, nebulization or enzymatic fragmentation in order to provide DNA fragments that are suitable for subsequent sequencing. The length of the fragments can be chosen based on the sequencing capacity of the sequencing platform that is subsequently used for sequencing. In some embodiments of the present disclosure, larger nucleic acid fragments are selected for isolation during the preparation of a library using the method described herein for selecting larger nucleic acid molecules, e.g. those with a tunable cut off value between 200 bp to 100 kbp.

The present disclosure is also directed to a kit including nanomembranes as described herein, a binding buffer as described herein and optionally a wash solution and an elution solution are included in the kit as also described herein. Typically, the kit contains silica nanomembranes and a binding buffer, wherein the binding buffer comprises alcohol and a chaotropic salt as also described herein. Typically, the alcohol is isopropyl alcohol. In certain embodiments, the binding buffer further comprises a molecular crowder such as polyvinylpyrrolidinone (PVP), PVP(Mw360,000)8000.

EXAMPLES

Example 1

This example demonstrates that a silica nanomembrane may be used to selectively recover double stranded DNA in a length dependent manner from a sample containing double stranded DNA of varying lengths. The size dependent recovery of DNA can be tuned to change the size dependence to smaller and larger DNA. This approach is applicable to adjust the DNA size distribution in a sample to a desired size range, for example in the preparation of sequencing libraries.

In this example, the input sample was 11.25 µl of a solution containing 200 ng/µl 148,502 bp linear DNA from bacteriophage lambda purchased from ThermoFisher and 100 ng/µl of a 100 bp plus dsDNA ladder (ThermoFisher Scientific Inc. part #SM0321). The sample was mixed in a 1.5 ml tube with 7.5 ul of binding buffer (8 M GuHCl, 10 mM Tris-HCl pH=7.5, 1 mM EDTA) and 100% isopropanol and TE (10 mM Tris-HCl, pH=8, 1 mM EDTA) such that the final isopropanol concentration was between 45 and 40% and the final volume was 60 ul. A circular silica nanomembrane with a diameter of 3 millimeter (mm) was added to the solution and mixed for 10 minutes on a Hula mixer (ThermoFisher cat #15920D). After mixing, the solution was removed, leaving the silica nanomembrane in the microcentrifuge tube. 500 µl of a primary wash buffer (50% EtOH, 25 mM NaCl, 10 mM Tris-HCl pH=9, 1 mM EDTA) was added to the tube containing the silica nanomembrane and the tube was inverted 7 times. This primary wash buffer was then removed from the microcentrifuge tube, leaving the silica nanomembrane. 30 µl Elution Buffer (10 mM Tris-HCl, pH=9, 0.1 mM EDTA) was added and the tube was left at room temperature for 10 minutes to elute the DNA.

Figure 3:
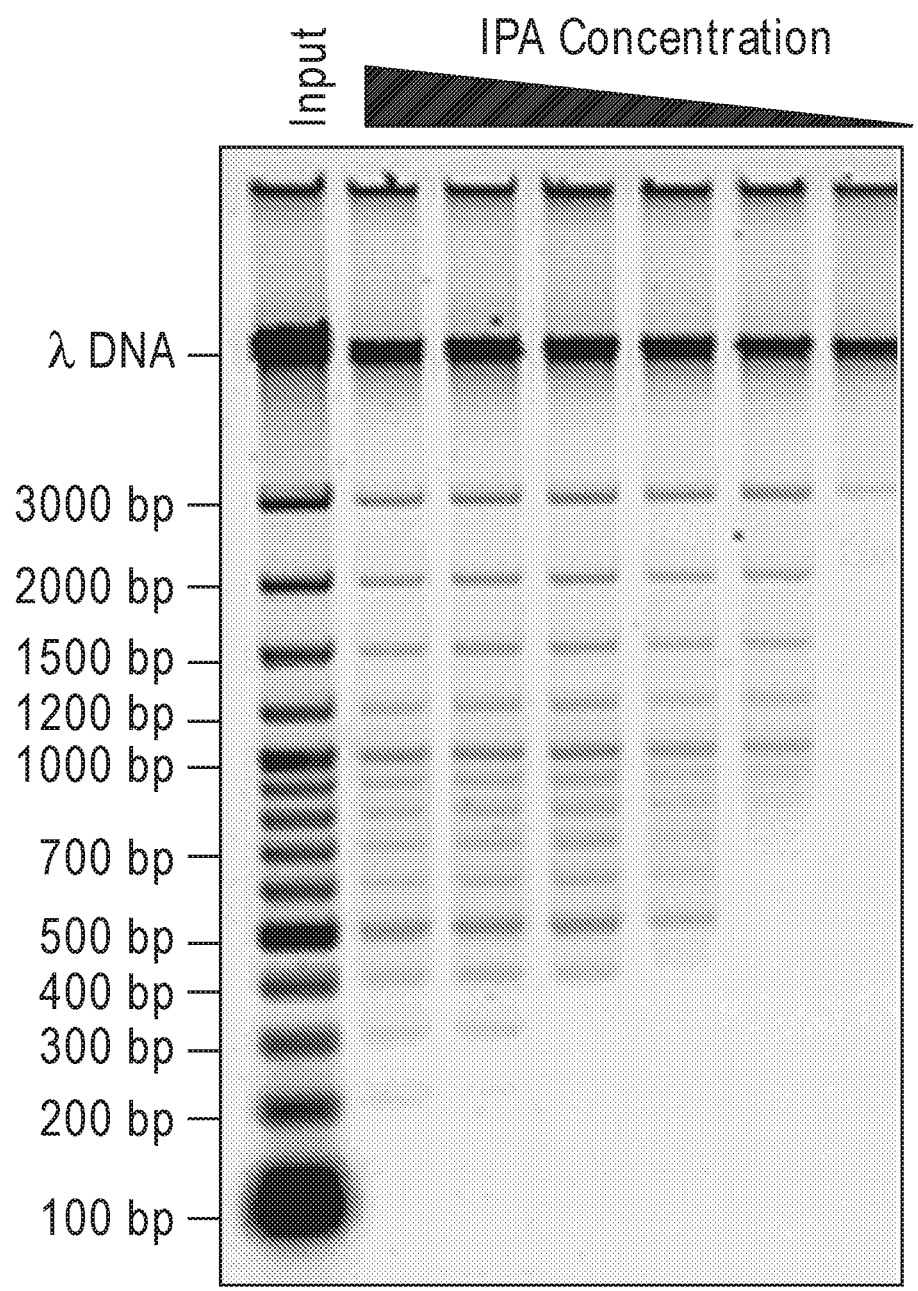
FIG. 3 depicts the size-dependent recovery of double stranded DNA (dsDNA) using a silica nanomembrane isolation method with different isopropyl alcohol (IPA) concentrations in the binding buffer as described in Example 1.

The recovered DNA run on a 1% agarose gel is shown in FIG. 3. As is evident from FIG. 3, there is a significant difference in length dependent recovery as the isopropanol % changes. The DNA cutoff (defined as the highest Mw band that has 10% or lower recovery) changes from 300 bp to 3000 bp as isopropanol concentration is reduced from 45 to 40%.

Example 2

In this example, a silica nanomembrane is used to recover longer double stranded DNA while removing short, single stranded or double stranded DNA oligomers. This approach is applicable for the removal of unused single stranded primers from PCR amplification reactions or unused single stranded or double stranded adapters from ligation reactions.

In this example, the input sample was 25 µl of a solution containing either 1) 100 ng/µl genomic DNA extracted from cultured GM12878 cells and 20 nM of an Alexa647-labeled 20 nt long single stranded DNA oligo or 2) 100 ng/µl genomic DNA extracted from cultured GM12878 cells and 20 nM of an Alexa647-labeled 20 bp long double stranded DNA oligo. 3.57 µl of binding buffer (8 M GuHCl, 10 mM Tris-HCl pH=7.5, 1 mM EDTA) was added to the samples in a 1.5 ml microcentrifuge tube and mixed by tapping. 28.57 µl of 100% isopropanol and one 3 mm diameter silica nanomembrane was then added to the tube and mixed on a Hula mixer (ThermoFisher cat #15920D) for 10 minutes. After mixing, the solution was removed, leaving the silica nanomembrane in the microcentrifuge tube. 500 µl of a wash buffer (60% EtOH, 50 mM NaCl 10 mM Tris-HCl pH=7.5, 1 mM EDTA) was added and the tube was inverted 7 times. This secondary wash buffer was then removed from the microcentrifuge tube, leaving the silica nanomembrane. 25 µl Elution Buffer (10 mM Tris-HCl, pH=9, 0.1 mM EDTA) was added and the tube was left at RT for 10 minutes to elute the DNA.

Figure 4:
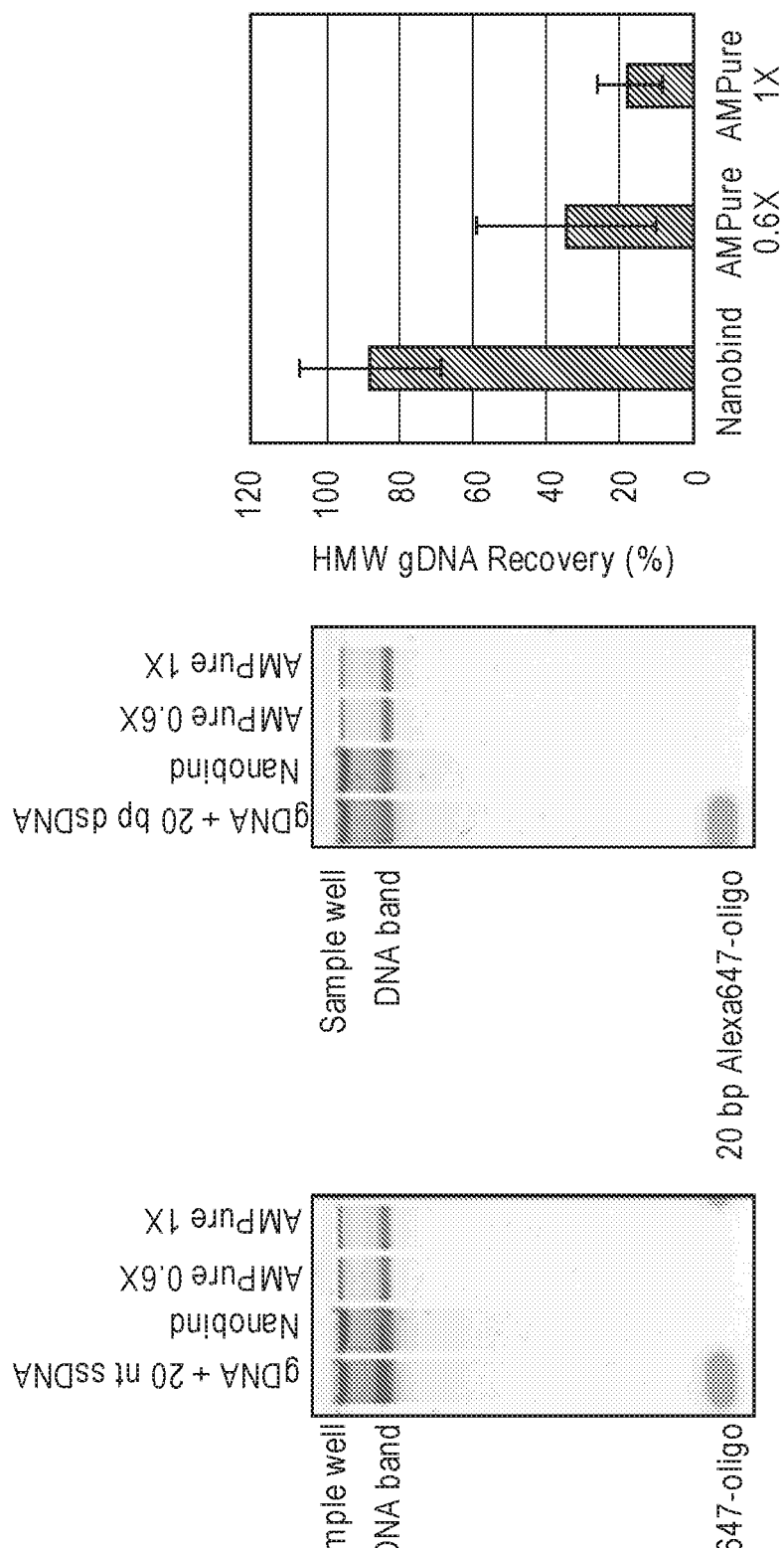
FIG. 4A depicts the effectiveness of removing Cy5-labeled single stranded oligonucleotides (20 nucleotides in length) from high molecular weight (MW) genomic DNA (gDNA) (50 kb-300 kb) using NANOBIND™ in comparison to the removal of the oligonucleotides using 0.6× and 1× AMPURE® beads as described in Example 2. Both methods effectively removed the oligonucleotides to undetectable levels.
FIG. 4B depicts the effectiveness of removing Cy5-labeled double stranded oligonucleotides (20 base pairs in length) from high molecular weight (MW) genomic DNA (gDNA) (50 kb-300 kb) using NANOBIND™ in comparison to the removal of the oligonucleotides using 0.6× and 1× AMPURE® beads as described in Example 2. Both methods effectively removed the oligonucleotides to undetectable levels.
FIG. 4C depicts quantification of DNA recovery by the QUBIT™ quantitation assay showing that NANOBIND™ has high recovery efficiency compared to AMPURE® beads, which have lower recovery efficiency for high molecular weight DNA at the concentration used, 100 ng/μl. See Example 2.

The results from this example are shown in FIG. 4. FIG. 4 4A) shows the size selected samples after being run on 1% Agarose gel. Each gel image compares the input sample (left lane) against an AMPURE® purified sample (0.6× and 1× beads standard protocol) and a NANOBIND™ size select purified sample. The upper bands represent gDNA stained with SYBR® safe intercalating dye. Both AMPURE® purification and NANOBIND™ size select showed recovery of the large gDNA. The lower bands represent the Alexa647-labeled 20 nt single stranded DNA oligo (FIG. 4A) or the Alexa647-labeled 20 bp double stranded DNA oligo (FIG. 4B). These can be seen in both input lanes but cannot be seen in the purified samples demonstrating that both NANOBIND™ and AMPURE® are effective at removing these short, single stranded DNA oligomers. Thus, a silica nanomembrane can be used to remove short single stranded oligomers, such as amplification primers or adapters, from reaction mixtures. FIG. 4C) shows the overall recovery from the silica nanomembrane and AMPURE® purification. The recovery from a silica nanomembrane purification is 88±20% whereas the recovery from AMPURE® purification is significantly lower at 34±24% for 0.6× and 17±8% for 1×.

Example 3

In this example, a silica nanomembrane is used to recover longer double stranded DNA while removing double stranded DNA below a variable cutoff length. The recovered DNA cutoff length is varied by changing the washing conditions of the NANOBIND™ rather than the initial binding conditions. This has utility for removing small dsDNA from reaction mixtures such as in sequencing library preparation to bias the DNA libraries to longer read lengths or to remove dsDNA adapters after a blunt end ligation step.

In this example, the input sample was 11.25 µl of a solution containing 200 ng/µl 48,502 bp linear DNA from bacteriophage lambda purchased from ThermoFisher and 100 ng/µl of a 100 bp plus dsDNA ladder (ThermoFisher Scientific Inc. part #SM0321).

The sample was mixed in a 1.5 ml tube with 7.5 ul of binding buffer (8 M GuHCl, 10 mM Tris-HCl pH=7.5, 1 mM EDTA) and 100% isopropanol and TE (10 mM Tris-HCl, pH=8, 1 mM EDTA) such that the final isopropanol concentration was 45% and the final volume was 60 ul. A circular silica nanomembrane with a diameter of 3 millimeter (mm) was added to the solution and mixed for 10 minutes on a Hula mixer (ThermoFisher cat #15920D). After mixing, the solution was removed, leaving the silica nanomembrane in the microcentrifuge tube. 500 µl of a wash buffer (60% EtOH, 0 or 25 or 50 or 100 or 500 mM NaCl, 10 mM Tris-HCl pH=9, 1 mM EDTA) was added to the tube containing the silica nanomembrane and the tube was inverted 7 times. This wash buffer was then removed from the microcentrifuge tube, leaving the silica nanomembrane. 30 µl Elution Buffer (10 mM Tris-HCl, pH=9, 0.1 mM EDTA) was added and the tube was left at room temperature for 10 minutes to elute the DNA.

Figure 5:
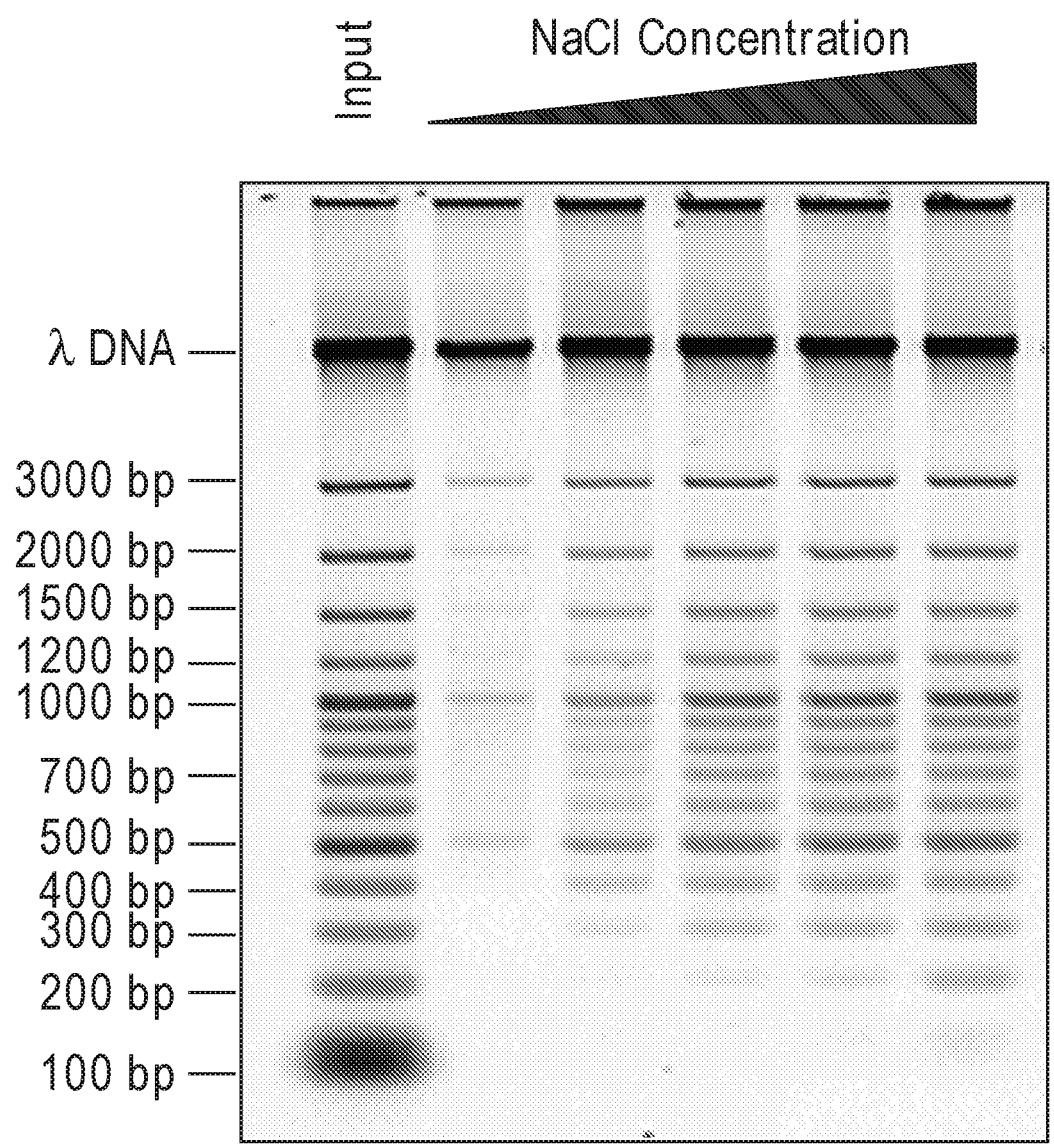
FIG. 5 depicts the size-dependent recovery of double stranded DNA (dsDNA) using a silica nanomembrane isolation method with the same binding conditions, but different NaCl concentrations in the wash step as described in Example 3. The left lane is the input sample, containing lambda DNA plus a 100 bp plus ladder (100-3000 bp). The size cut-off is increased to larger DNA with decreasing NaCl in the washing buffer.

The recovered DNA run on a 1% agarose gel is shown in FIG. 5. As is evident from FIG. 5, there is a significant difference in length dependent recovery as the NaCl in the wash changes. The DNA cutoff (defined as the highest Mw band that has 10% or lower recovery) changes from 100 bp to 1500 bp as NaCl concentration in the wash is increased from 0 to 500 mM.

Example 4

In this example, a silica nanomembrane is used to recover shorter (<1000 bp) dsDNA while removing long double stranded DNA from DNA mixtures and unused single stranded primers. This example demonstrates that the present method can be used to purify amplicons from PCR amplifications of, for example, kilobase- to megabase-pair gDNA.

In this example the input sample was 12.5 µl of a mixture containing 40 nM of a 50 bp ladder (Thermo Fisher Scientific Inc. part #SM0371), 140 ng/µl of linearized lambda phage DNA (48 kbp length, purchased from Thermo Fisher Scientific Inc.) and 20 nM of Alexa647-labeled, 20 nt long DNA oligomer.

25 µl of binding buffer containing 1.5 M GuHCl and pH of either 9, 10, 11, 12, or 13 was added to the samples in a 1.5 ml microcentrifuge tube and mixed by tapping. 37.5 µl of 100% isopropanol and one 3 mm diameter silica nanomembrane was then added to each tube and mixed by tapping. This was left for 20 minutes to allow the DNA to bind. After 20 minutes, the solution was removed, leaving the silica nanomembrane in the microcentrifuge tube. 500 µl of a primary wash buffer (70% EtOH, 0.5 M GuHCl, 10 mM Tris-HCl pH=7.5, 1 mM EDTA) was added to the tube containing the silica nanomembrane and the tube was inverted 5-10 times. This primary wash buffer was then removed from the microcentrifuge tube, leaving the silica nanomembrane. 500 µl of a secondary wash buffer (70% EtOH, 50 mM NaCl 10 mM Tris-HCl pH=7.5, 1 mM EDTA) was added and the tube was inverted 5-10 times. This secondary wash buffer was then removed from the microcentrifuge tube, leaving the silica nanomembrane. 50 µl of water was added, and the tube was left at 55° C. for 20 minutes to elute the DNA.

Figure 6:
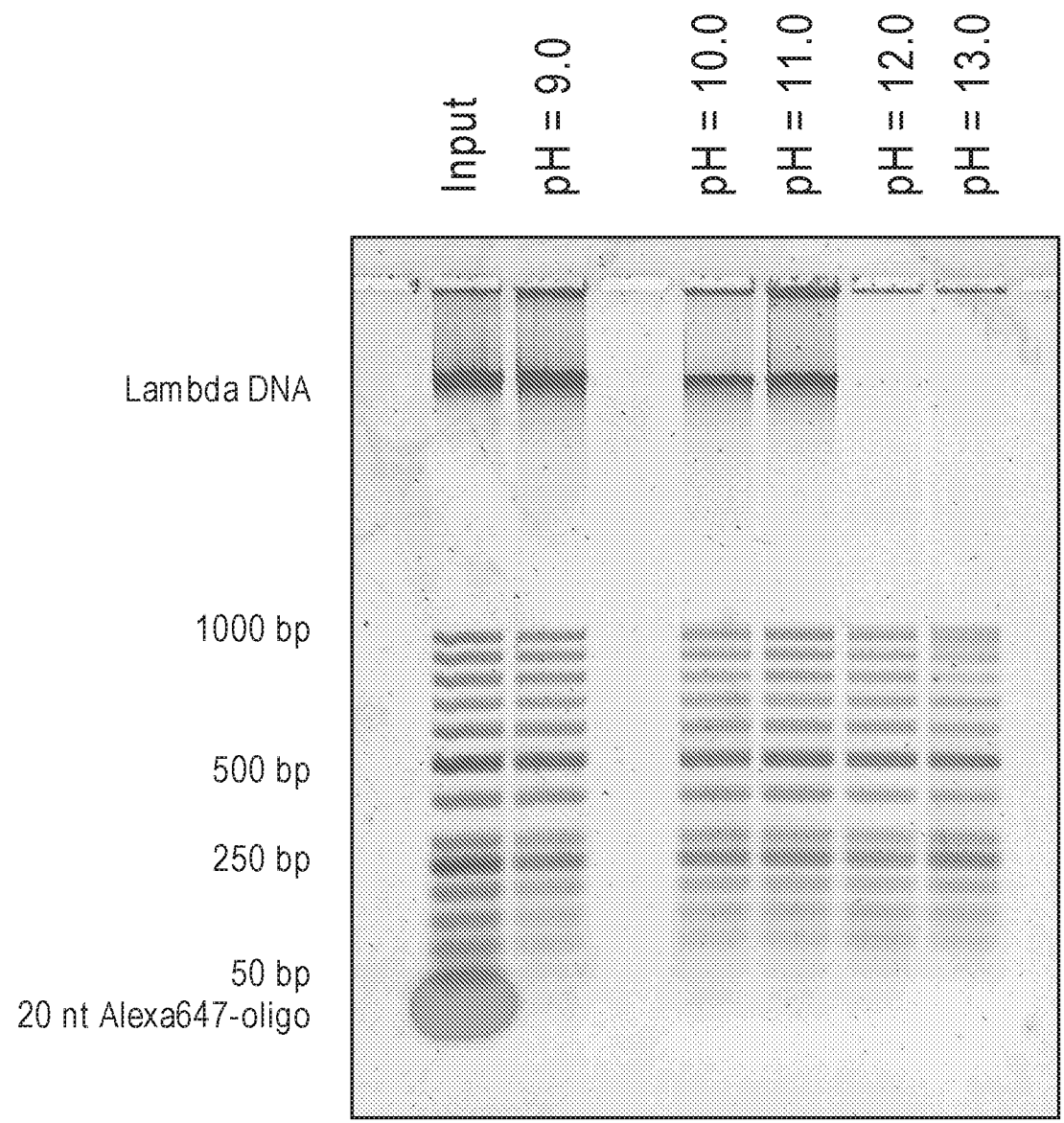
FIG. 6 depicts the input DNA (left lane) and recovered DNA (right lanes) from NANOBIND™ size selection purifications performed at pH=9, 10, 11, 12 and 13 (from $2^{nd}$ left lane, left to right) as described in Example 4. The green colored bands show lambda DNA and a 50 bp ladder stained with the SYBR® Gold intercalating dye. The red colored bands show fluorescence from the Alexa647 labeled 20 nucleotide (nt) ssDNA oligonucleotide (oligo). After NANOBIND™ size selection purification, the intensity of the red bands decreases significantly, showing that NANOBIND™ is effective at removing these short, single stranded DNA oligomers. The lambda DNA bands are absent in purifications performed at pH=12 and 13, showing that the purification efficiently removes longer dsDNA as well.

FIG. 6 shows the input sample and NANOBIND™ size select purified DNA using binding buffers with pH=9, 10, 11, 12 and 13. Non labeled DNA was stained with the SYBR® Gold intercalating dye. The 20 nt oligo was labeled with Alexa647 dye. In the NANOBIND™ size select purified samples, the Alexa647 oligo is nearly entirely removed, showing that a silica nanomembrane is effective at removing short, single stranded DNA oligomers. The lambda DNA bands are absent in purifications performed at pH=12 and 13, showing that the purification at high pH effectively removes longer dsDNA as well.

Example 5

In this example, double stranded DNA is recovered above a tunable cutoff size between 1000 and 10000 bp. The cutoff size is defined as the highest Mw band that has 10% or lower recovery. This protocol is of utility for third generation long read sequencing, where it can be used instead of the time- and sample-consuming BLUE PIPPIN™ size selection instrument.

In this example, the input sample was 25 µl of a mixture containing 100 ng/µl of a 1 kbp plus ladder (Thermo Fisher Scientific Inc. part #SM1331) and 200 ng/µl of 48,502 bp linear DNA from bacteriophage lambda purchased from ThermoFisher.

7.5 µl of 5M NaCl and 25 µl of 2× PVP (Mw=360,000) solution were added to the samples and mixed by tapping. The 2× PVP solutions were 10, 8, 6, 4, 3.5 and and 3% wt/vol Polyvinylpyrrolidone (Mw=360,000) (Sigma Aldrich part #PVP360-100G) solutions. The resultant solutions were centrifuged at 8000 g and room temperature for 30 minutes. The supernatant was removed, leaving a DNA pellet. Next, 200 µl of 70% EtOH was added to the tube and centrifuged at 8000 g at room temperature for 2 minutes. The EtOH supernatant was removed, and the DNA pellet was dried by leaving the microcentrifuge tube open at room temperature for 2 minutes. The pellet was re-suspended in 25 µl of Elution Buffer (10 mM Tris-HCl, pH=9, 0.1 mM EDTA) and incubated at room temperature for 10 minutes, tapping intermittently.

This example demonstrates the pelleting step part of the NANOBIND™ large size selection process as described herein.

Figures 7A, 7B:
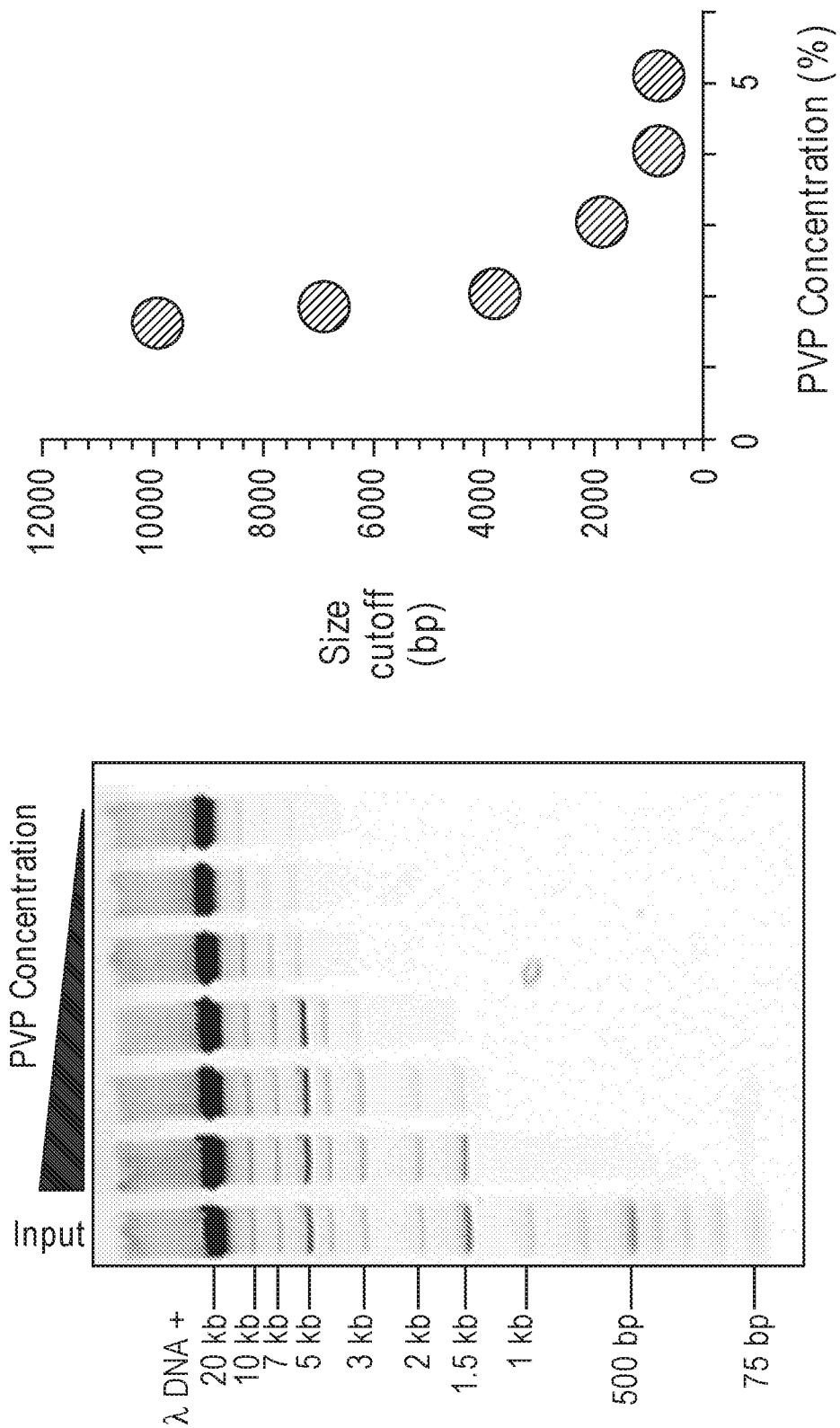
FIG. 7A depicts NANOBIND™ size selection purification of λ DNA spiked with a 1 kb plus ladder as described in Example 5 using a large nucleic acid size select method as described herein. The large nucleic acid size select method was performed using polyvinylpyrrolidone (PVP)-driven precipitation. PVP acts as a molecular crowder to tune nucleic acid precipitation by length.
FIG. 7B depicts the cutoff size (defined as the highest Mw band that has 10% or lower recovery) that was tunable from 1000 bp-10 kb by changing PVP concentration. See Example 5.

As is evident from FIG. 7, there is a significant difference in length dependent recovery as the PVP concentration in the pelleting buffer changes. The DNA cutoff (defined as the highest Mw band that has 10% or lower recovery) changes from 1000 bp to 10000 bp as PVP concentration in the buffer is decreased from 5 to 1.5%.

Example 6

This example demonstrates how a silica nanomembrane may be used to clean up a PCR amplification reaction by recovering PCR amplification products while removing primers, dNTPs, and enzymes.

The input sample was a 12.5 µl of a mixture containing target DNA, DNA primer oligomers, dNTPs and polymerase. The reaction was heat cycled through denaturation, annealing and extension steps to produce DNA amplicons. 25 µl of binding buffer (6M Guanadinium Hydrochloride, 10 mM Tris-HCl, pH=6.8, 1 mM EDTA), one silica nanomembrane and 37.5 µl of 100% isopropanol were added to the PCR amplified sample. This was then mixed and left for 1 hour, after which, all liquid was removed from the tube, leaving the silica nanomembrane. 700 µl of a primary wash buffer (70% EtOH, 0.5 M GuHCl, 10 mM Tris-HCl pH=7.5, 1 mM EDTA) was added and the tube was inverted 5-10 times. This primary wash buffer was then removed from the microcentrifuge tube, leaving the silica nanomembrane. 500 µl of a secondary wash buffer (70% EtOH, 50 mM NaCl 10 mM Tris-HCl pH=7.5, 1 mM EDTA) was then added and the tube was inverted 5-10 times. This secondary wash buffer was then removed from the microcentrifuge tube, leaving the silica nanomembrane. 50 µl elution buffer was added and the tube was left at 55° C. for 10 minutes to elute the DNA. The eluate contains the PCR amplicons, but the dNTPs and primers were reduced to lower than 0.2% of their input masses.

Figure 8:
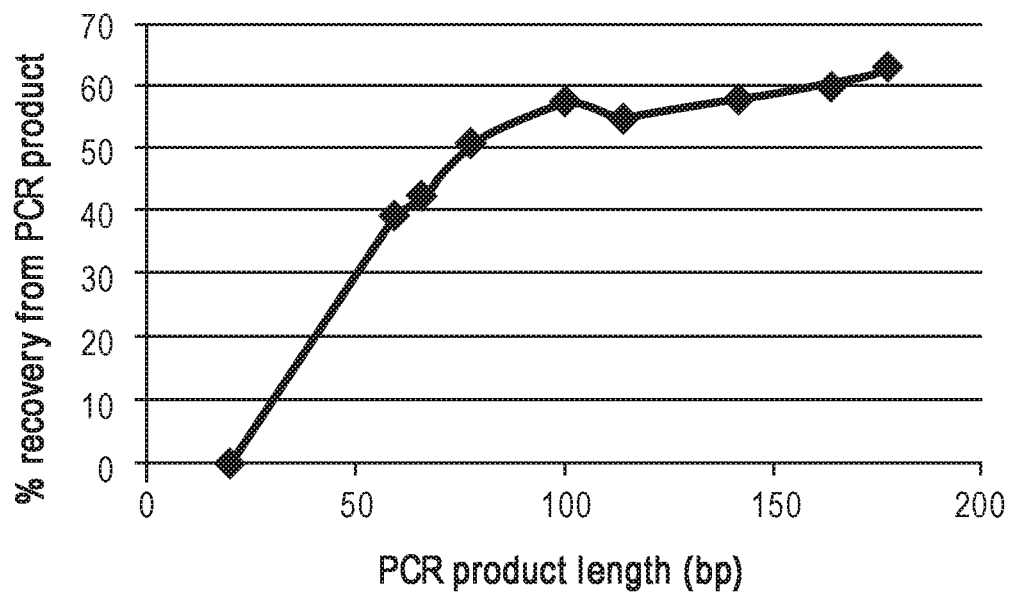
FIG. 8 depicts the size-dependent recovery of dsDNA PCR products using the NANOBIND™ size selection purification method as described in Example 6.

The recoveries for silica nanomembrane purification are shown in FIG. 8. As is evident from the figure, there is a length dependence in product recovery, with shorter products being recovered with lower efficiency than longer products.

REFERENCES

1. J. Eid, A. Fehr, J. Gray, K. Luong, J. Lyle, G. Otto, P. Peluso, D. Rank, P. Baybayan, B. Bettman, A. Bibillo, K. Bjornson, B. Chaudhuri, F. Christians, R. Cicero, S. Clark, R. Dalal, A. Dewinter, J. Dixon, M. Foquet, A. Gaertner, P. Hardenbol, C. Heiner, K. Hester, D. Holden, G. Kearns, X. Kong, R. Kuse, Y. Lacroix, S. Lin, P. Lundquist, C. Ma, P. Marks, M. Maxham, D. Murphy, I. Park, T. Pham, M. Phillips, J. Roy, R. Sebra, G. Shen, J. Sorenson, A. Tomaney, K. Travers, M. Trulson, J. Vieceli, J. Wegener, D. Wu, A. Yang, D. Zaccarin, P. Zhao, F. Zhong, J. Korlach, S. Turner, Real-Time DNA Sequencing from Single Polymerase Molecules. *Science* 323, 133 (Jan. 2, 2009).
2. M. Jain, H. E. Olsen, B. Paten, M. Akeson, The Oxford Nanopore MinION: delivery of nanopore sequencing to the genomics community. *Genome Biology* 17, 239 (Nov. 25, 2016).
3. G. X. Zheng, B. T. Lau, M. Schnall-Levin, M. Jarosz, J. M. Bell, C. M. Hindson, S. Kyriazopoulou-Panagiotopoulou, D. A. Masquelier, L. Merrill, J. M. Terry, P. A. Mudivarti, P. W. Wyatt, R. Bharadwaj, A. J. Makarewicz, Y. Li, P. Belgrader, A. D. Price, A. J. Lowe, P. Marks, G. M. Vurens, P. Hardenbol, L. Montesclaros, M. Luo, L. Greenfield, A. Wong, D. E. Birch, S. W. Short, K. P. Bjornson, P. Patel, E. S. Hopmans, C. Wood, S. Kaur, G. K. Lockwood, D. Stafford, J. P. Delaney, I. Wu, H. S. Ordonez, S. M. Grimes, S. Greer, J. Y. Lee, K. Belhocine, K. M. Giorda, W. H. Heaton, G. P. McDermott, Z. W. Bent, F. Meschi, N. O. Kondov, R. Wilson, J. A. Bernate, S. Gauby, A. Kindwall, C. Bermejo, A. N. Fehr, A. Chan, S. Saxonov, K. D. Ness, B. J. Hindson, H. P. Ji, Haplotyping Germline and Cancer Genomes with High-Throughput Linked-Read Sequencing. *Nature biotechnology* 34, 303 (March, 2016).
4. E. T. Lam, A. Hastie, C. Lin, D. Ehrlich, S. K. Das, M. D. Austin, P. Deshpande, H. Cao, N. Nagarajan, M. Xiao, P. Y. Kwok, Genome Mapping on Nanochannel Arrays for Structural Variation Analysis and Sequence Assembly. *Nature biotechnology* 30, 771 (August, 2012).
5. Y. Zhang, Y. Zhang, J. M. Burke, K. Gleitsman, S. M. Friedrich, K. J. Liu, T.-H. Wang, A Simple Thermoplastic Substrate Containing Hierarchical Silica Lamellae for High-Molecular-Weight DNA Extraction. *Advanced Materials*, 28(48), 10810 (2016).
6. L. Liu, Z. Guo, Z. Huang, J. Zhuang, W. Yang, Size-selective separation of DNA fragments by using lysine-functionalized silica particles. *Scientific Reports*, 6, 22029, (2016).
7. Based on Quoted Costs from Fraunhofer Fep (Dresden, Germany), Deposition Technology Innovations (Jeffersonville, Ind.), and Sigma Technologies (Tuscon, Ariz.).
8. K. A. Melzak, C. S. Sherwood, R. F. B. Turner, C. A. Haynes, Driving Forces for DNA Adsorption to Silica in Perchlorate Solutions. *Journal of Colloid and Interface Science* 181, 635 (1996).
9. H. Tian, A. F. Huhmer, J. P. Landers, Evaluation of Silica Resins for Direct and Efficient Extraction of DNA from Complex Biological Matrices in a Miniaturized Format. *Anal Biochem* 283, 175 (Aug. 1, 2000).
10. P. E. Vandeventer, J. S. Lin, T. J. Zwang, A. Nadim, M. S. Johal, A. Niemz, Multiphasic DNA Adsorption to Silica Surfaces under Varying Buffer, Ph, and Ionic Strength Conditions. *J Phys Chem B* 116, 5661 (May 17, 2012).
11. H. X. Zhou, G. Rivas, A. P. Minton, Macromolecular Crowding and Confinement: Biochemical, Biophysical, and Potential Physiological Consequences. *Annual review of biophysics* 37, 375 (2008).
12. E. Raspaud, M. Olvera de la Cruz, J.-L. Sikorav, F. Livolant, Precipitation of DNA by Polyamines: A Polyelectrolyte Behaviour. *Biophysical Journal* 74, 381 (1998).
13. R. J. Ellis, Macromolecular Crowding: Obvious but Underappreciated. *Trends in biochemical sciences* 26, 597 (October, 2001).

We claim:

1. A method of size selecting nucleic acids, the method comprising:
   a. adding a precipitation solution comprising water, salt, and polyvinylpyrrolidone (PVP) and/or Ficoll to a nucleic acid-containing sample to produce a sample-solution;
   b. allowing nucleic acids of one or more selected sizes in the nucleic acid-containing sample to precipitate driven by the PVP and/or the Ficoll to produce precipitated nucleic acids; and,
   c. size selecting nucleic acids by separating the precipitated nucleic acids from the nucleic acid remaining in solution,
   wherein the method lacks a separate magnetic bead purification step.

2. The method of claim 1, comprising tuning at least one condition of the precipitation solution to determine a selected size cutoff value, wherein the condition is selected from the group consisting of: PVP and/or Ficoll concentration, PVP molecular weight, presence or absence of chaotropic salts, presence or absence of monovalent and/or divalent salts, salt concentration and type, alcohol type and concentration, presence or absence of polyamines, presence or absence of denaturing agents, presence or absence of other additive molecules, pH, precipitation/binding time, precipitation/binding temperature, precipitation/binding volume, centrifugation time, centrifugation temperature, and combinations thereof.

3. The method of claim 1, wherein the precipitated nucleic acids comprise all sizes above a cutoff value.

4. The method of claim 1, comprising performing steps a)-c) prior to performing a nanomembrane purification method.

5. The method of claim 1, comprising performing steps a)-c) after performing a nanomembrane purification method.

6. The method of claim 1, comprising performing steps a)-c) concurrently with performing a nanomembrane purification method.

7. The method of claim 1, wherein the precipitated nucleic acids comprise nucleic acids of a desired size range.

8. The method of claim 7, comprising re-suspending the pelleting precipitated nucleic acids.

9. The method of claim 1, comprising pelleting the nucleic acids in the nucleic acid-containing sample based on the size to produce a nucleic acid pellet.

10. The method of claim 9, further comprising adding alcohol to the nucleic acid pellet, centrifuging the nucleic acid pellet, and removing alcohol supernatant from the nucleic acid pellet.

11. The method of claim 1, wherein the PVP comprises PVP(Mw29,000), PVP(Mw40,000), PVP(Mw55,000), PVP(Mw360,000), and/or PVP(Mw1,300,000).

12. The method of claim 1, wherein a concentration of the PVP in the sample-solution is such that the one or more selected sizes of the nucleic acids is from 1000 base pairs to 10 kilobases.

13. The method of claim 1, wherein steps a)-c) are performed separate from a nanomembrane purification method.

14. The method of claim 1, comprising size selecting the nucleic acids at a nucleic acid concentration greater than 50 ng/µl in the sample-solution.

15. The method of claim 1, wherein the method further lacks a separate pulsed field gel electrophoresis (PFGE) purification step.

16. A method of size selecting nucleic acids, the method comprising:
   a. adding a precipitation solution comprising water, salt, and polyvinylpyrrolidone (PVP) and/or Ficoll to a nucleic acid-containing sample in a tube to produce a sample-solution;
   b. centrifuging the sample-solution to produce a nucleic acid pellet in the tube, wherein the nucleic acid pellet comprises nucleic acids of one or more selected sizes that precipitate driven by the PVP and/or the Ficoll and wherein a supernatant comprises nucleic acids remaining in solution;
   c. removing the supernatant from the tube; and,
   d. re-suspending the nucleic acid pellet in an aqueous solution,
   wherein the method lacks a separate magnetic bead purification step.

17. The method of claim 16, comprising tuning at least one condition of the precipitation solution to determine a selected size cutoff value, wherein the condition is selected from the group consisting of: PVP and/or Ficoll concentration, PVP molecular weight, presence or absence of chaotropic salts, presence or absence of monovalent and/or divalent salts, salt concentration and type, alcohol type and concentration, presence or absence of polyamines, presence or absence of denaturing agents, presence or absence of other additive molecules, pH, precipitation/binding time, precipitation/binding temperature, precipitation/binding volume, centrifugation time, centrifugation temperature, and combinations thereof.

18. The method of claim 16, wherein the precipitated nucleic acids comprise all sizes above a cutoff value.

19. The method of claim 16, comprising performing steps a)-d) prior to performing a nanomembrane purification method.

20. The method of claim 16, comprising performing steps a)-d) after performing a nanomembrane purification method.

21. The method of claim 16, comprising performing steps a)-d) concurrently with performing a nanomembrane purification method.

22. The method of claim 16, further comprising adding alcohol to the tube, centrifuging the tube, and removing alcohol supernatant from the tube after performing step c).

23. The method of claim 16, wherein the precipitation solution further comprises a buffer.

24. The method of claim 16, wherein the aqueous solution comprises an elution buffer.

25. The method of claim 16, wherein the PVP comprises PVP(Mw29,000), PVP(Mw40,000), PVP(Mw55,000), PVP(Mw360,000), and/or PVP(Mw1,300,000).

26. The method of claim 16, wherein a concentration of the PVP in the sample-solution is such that the one or more selected sizes of the nucleic acids is from 1000 base pairs to 10 kilobases.

27. The method of claim 16, wherein steps a)-c) are performed separate from a nanomembrane purification method.

28. The method of claim 16, comprising size selecting the nucleic acids at a nucleic acid concentration greater than 50 ng/µl in the sample-solution.

29. The method of claim 16, wherein the method further lacks a separate pulsed field gel electrophoresis (PFGE) purification step.

30. A method of size selecting nucleic acids, the method comprising:
   a. adding a precipitation solution comprising water, salt, and polyvinylpyrrolidone (PVP) to a nucleic acid-containing sample to produce a sample-solution, wherein the PVP has a molecular weight from 10,000 to 1,300,000 and wherein a concentration of the PVP in the precipitation solution is from 0.1% to 40%;
   b. allowing nucleic acids of one or more selected sizes in the nucleic acid-containing sample to precipitate driven by the PVP to produce precipitated nucleic acids; and,
   c. size selecting nucleic acids by separating the precipitated nucleic acids from the nucleic acid remaining in solution,
   wherein the method lacks a separate magnetic bead purification step.

31. The method of claim 30, wherein the precipitated nucleic acids comprise a size cutoff value of from 1000 bp to 10000 bp.

* * * * *